(12) United States Patent
Luo et al.

(10) Patent No.: US 11,713,359 B2
(45) Date of Patent: *Aug. 1, 2023

(54) APOLIPOPROTEIN NANODISCS WITH TELODENDRIMER

(71) Applicant: LAWRENCE LIVERMORE NATIONAL SECURITY, LLC, Livermore, CA (US)

(72) Inventors: Juntao Luo, Jamesville, NY (US); Wei He, Davis, CA (US); Kit S. Lam, Davis, CA (US); Paul Henderson, Dublin, CA (US); Matthew A. Coleman, Oakland, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 123 days.

This patent is subject to a terminal disclaimer.

(21) Appl. No.: 17/308,921

(22) Filed: May 5, 2021

(65) Prior Publication Data

US 2021/0317234 A1 Oct. 14, 2021

Related U.S. Application Data

(63) Continuation of application No. 15/499,855, filed on Apr. 27, 2017, now Pat. No. 11,053,322, which is a continuation of application No. 13/719,785, filed on Dec. 19, 2012, now Pat. No. 9,644,038.

(60) Provisional application No. 61/578,583, filed on Dec. 21, 2011.

(51) Int. Cl.
C07K 17/02 (2006.01)
C07K 14/775 (2006.01)

(52) U.S. Cl.
CPC ............ *C07K 17/02* (2013.01); *C07K 14/775* (2013.01)

(58) Field of Classification Search
None
See application file for complete search history.

(56) References Cited

U.S. PATENT DOCUMENTS

| | | | |
|---|---|---|---|
| 5,679,559 | A | 10/1997 | Kim et al. |
| 9,644,038 | B2 * | 5/2017 | Luo ................. C07K 14/775 |
| 10,934,628 | B2 | 3/2021 | Hoeprich, Jr. et al. |
| 11,053,322 | B2 | 7/2021 | Luo et al. |
| 11,207,422 | B2 | 12/2021 | Coleman et al. |
| 11,279,749 | B2 | 3/2022 | Hoeprich, Jr. et al. |
| 11,300,572 | B2 | 4/2022 | Coleman et al. |
| 2004/0204354 | A1 | 10/2004 | Nelson et al. |
| 2006/0088524 | A1 | 4/2006 | Morrissey et al. |
| 2006/0127467 | A1 | 6/2006 | Watkin |
| 2018/0079829 | A1 | 3/2018 | Luo et al. |
| 2022/0211866 | A1 | 7/2022 | Coleman et al. |
| 2022/0283171 | A1 | 9/2022 | Coleman et al. |

OTHER PUBLICATIONS

Final Office Action for U.S. Appl. No. 16/082,924, filed Sep. 6, 2018 on behalf of Lawrence Livermore National Security, LLC dated Jan. 25, 2022. 21 pages.
Bezrukov S. M. "Functional consequences of lipid packing stress" Current Opinion in Colloid & Interface Science 5, Jan. 2000, pp. 237-243.
Denisov I. G. "Thermotropic Phase Transition in Soluble Nanoscale Lipid Bilayers" J Phys Chem B., Aug. 18, 2005, 109(32), pp. 15580-15588. 23 pages.
Final Office Action for U.S. Appl. No. 15/755,018, filed Feb. 23, 2018 on behalf of Lawrence Livermore National Security, LLC dated Dec. 27, 2021. 18 pages.
Klevens H. B. "Structure and Aggregation in Dilute Solutions of Surface Active Agents" The Journal of the American Oil Chemists Society, Feb. 1953, pp. 74-80. 7 pages.
Liposome—Wikipedia, the free encyclopedia. Downloaded through The Wayback Machine with a date of Dec. 31, 2015. 7 pages. web.archive.org/web/20151231050831/https://en.wikipedia.org/wiki/Lipsome.
Martinez D. et al., "Lipid Internal Dynamics Probed in Nanodiscs" Chem Phys Chem, Jan. 2017, 18, pp. 2651-2657.
Notice of Allowability for U.S. Appl. No. 16/159,189, filed Oct. 12, 2018, on behalf of Lawrence Livermore National Security, LLC. dated Dec. 21, 2021. 4 Pages.
Notice of Allowance for U.S. Appl. No. 15/744,754, filed Jan. 12, 2018 on behalf of Lawrence Livermore National Security, LLC. dated Nov. 22, 2021. 11 pages.
Notice of Allowance for U.S. Appl. No. 16/159,189, filed Oct. 12, 2018 on behalf of Lawrence Livermore National Security, LLC. dated Dec. 9, 2021. 10 Pages.
Notice of Allowance for U.S. Appl. No. 16/609,420, filed Oct. 29, 2019 on behalf of Lawrence Livermore National Laboratory. dated Nov. 10, 2021. 7 Pages.
Pollock, N.L. et al., "Structure and function of membrane proteins encapsulated in a polymer-bound lipid bilayer", Biochimica et Biophysica Acta (BBA)—Biomembranes (Apr. 2018), vol. 1860, Issue 4, pp. 809-817, 9 pages; Internet: dx.doi.org/10.1016/j.bbamem.2017.08.012.
Restriction Requirement for U.S. Appl. No. 15/969,311, filed May 2, 2018 on behalf of Lawrence Livermore National Security, LLC. dated Dec. 20, 2021. 9 Pages.

(Continued)

*Primary Examiner* — Anand U Desai
(74) *Attorney, Agent, or Firm* — Steinfl + Bruno, LLP

(57) ABSTRACT

The present invention provides a nanodisc with a membrane scaffold protein. The nanodisc includes a membrane scaffold protein, a telodendrimer and a lipid. The membrane scaffold protein can be apolipoprotein. The telodendrimer has the general formula PEG-L-D-(R)$_n$, wherein D is a dendritic polymer; L is a bond or a linker linked to the focal point group of the dendritic polymer; each PEG is a poly(ethylene glycol) polymer, each R is and end group of the dendritic polymer, or and end group with a covalently bound hydrophobic group, hydrophilic group, amphiphilic compound, or drug; and subscript n is an integer from 2 to 20. Cell free methods of making the nanodiscs are also provided.

19 Claims, 14 Drawing Sheets

Specification includes a Sequence Listing.

(56) References Cited

OTHER PUBLICATIONS

Schachter T. et al., "Confinement in Nanodiscs Anisotropically Modifies Lipid Bilayer Elastic Properties" J. Phys. Chem. B, Jul. 2020, vol. 124, pp. 7166-7175.
Schuler M. et al., "Nanodiscs as a new tool to examine lipid-protein interactions" Methods Mol Biol., 2013; 974, pp. 415-433.
Shelby M. et al., "Cell-Free Co-Translational Approaches for Producing Mammalian Receptors: Expanding the Cell-Free Expression Toolbox Using Nanolipoproteins" Frontiers in Pharmacology, vol. 10 No. 744, Jul. 2019, pp. 1-12.
Sligar, "Protocols for Preparation of Nanodiscs", (Mar. 4, 2008), 7 pages.
Stepien P. et al., "Comparative EPR studies on lipid bilayer properties in nanodiscs and liposomes" Biochimica et Biophysica Acta, 1848, Oct. 2014, pp. 60-66.
Tanaka, M. et al. "Preparation and Characterization of Reconstituted Lipid-Synthetic Polymer Discoidal Particles" Langmuir, (2015), vol. 31, Issue 46, 12719-12726. 8 pages. Internet: doi.10.1021/acs.langmuir.5b03438.
"Drug" Wikipedia, the free encyclopedia. Downloaded through the Wayback Machine, dated Dec. 8, 2011. 5 pages.
Extended European Search Report for EP Application No. 17763807.9 filed on Oct. 4, 2018 on behalf of Lawrence Livermore National Security LLC dated Oct. 30, 2019. 8 pages.
Marsh D. "Equation of State for Phospholipid Self-Assembly" Biophysical Journal, vol. 110, Jan. 2016, pp. 188-196.
Non-Final Office Action for U.S. Appl. No. 15/755,018, filed Feb. 23, 2018, on behalf of Lawrence Livermore National Laboratory. dated Jul. 16, 2021. 22 pages.
Non-Final Office Action for U.S. Appl. No. 16/082,924, filed Sep. 6, 2018 on behalf of Lawrence Livermore National Security, LLC dated May 25, 2021. 25 pages.
Non-Final Office Action for U.S. Appl. No. 16/159,189, filed Oct. 12, 2018 on behalf of Lawrence Livermore National Security, LLC. dated Jun. 24, 2021. 32 pages.
Notice of Allowance for U.S. Appl. No. 15/744,754, filed Jan. 12, 2018, on behalf of Lawrence Livermore National Laboratory. dated Jul. 14, 2021. 11 pages.
Notice of Allowance for U.S. Appl. No. 16/609,420, filed Oct. 29, 2019 on behalf of Lawrence Livermore National Laboratory. dated Jul. 28, 2021. 7 pages.
Notice of Allowance for U.S. Appl. No. 16/609,420, filed Oct. 29, 2019 on behalf of Lawrence Livermore National Laboratory. dated May 6, 2021. 10 pages.
European Examination Report for EP Application No. 17763807.9 filed on Mar. 3, 2017 on behalf of Lawrence Livermore National Security, LLC dated Aug. 17, 2022 6 pages.
Final Office Action for U.S. Appl. No. 15/755,018, filed Feb. 23, 2018 on behalf of Lawrence Livermore National Security, LLC dated Nov. 17, 2022 20 pages.
Final Office Action for U.S. Appl. No. 15/969,311, filed May 2, 2018 on behalf of Lawrence Livermore National Security, LLC, dated Nov. 18, 2022, 9 pages.
Frankel D. et al., "Photoinduced destabilization of bilayer vesicles" J. Am. Chem. Soc. Vol. 111 No. 26, 1989, pp. 9262-9263.
Geall A. J. et al., "Nonviral delivery of self-amplifying RNA vaccines" PNAS, vol. 109 No. 36, Sep. 2012, pp. 14604-14609.
He, W. et al. "Cationic HDL mimetics enhance in vivo delivery of self-replicating mRNA", Nanomedicine, Feb. 2020; 24: 102154. 20 pages. Doi:10.1016/j.nano.2020.102154.
Houseley J. et al., "The Many Pathways of RNA Degradation" Cell, vol. 136, Feb. 2009, pp. 763-776.
Kauffman K. J. et al., "Materials for non-viral intracellular delivery of messenger RNA therapeutics" Journal of Controlled Release, vol. 240, 2016, pp. 227-234.
Lamparski H. et al., "Photoinduced destabilization of liposomes" Biochemistry, vol. 31 No. 3, 1992, pp. 685-694.
"Technical Bulletin: pSV-β Galactosidase Control Vector: Instructions for Use of Product E1081", Promega, Revised Sep. 2006. 9 pages. Website: www.promega.com.
Midoux P. et al. "Lipid-based mRNA vaccine delivery systems" Expert Rev. Vaccines, 2014, pp. 1-14.
Mueller A. et al., "Supramolecular materials via polymerization of mesophases of hydrated amphiphiles" Chem. Rev. 102(3), Mar. 2002, pp. 727-757. 64 pages.
Non-Final Office Action for U.S. Appl. No. 15/969,311, filed May 2, 2018, on behalf of Synthetic Genomics, Inc. dated Jun. 10, 2022. 55 Pages.
Non-Final Office Action for U.S. Appl. No. 16/082,924, filed Sep. 6, 2018 on behalf of Lawrence Livermore National Security, LLC dated Dec. 2, 2022 25 pages.
Pardi N. et al., "Expression kinetics of nucleoside-modified mRNA delivered in lipid nanoparticles to mice by various routes." J. Control Release, Nov. 2015, pp. 1-18.
Pardi N. et al., "mRNA vaccines—a new era in vaccinology" Nature Reviews, vol. 17, Apr. 2018, pp. 261-279.
Ramachandran S. et al., "Delivery Strategies for mRNA Vaccines" Pharmaceutical Medicine, vol. 36, Jan. 2022, pp. 11-20.
Reichmuth A. M. et al., "mRNA vaccine delivery using lipid nanoparticles" Ther. Deliv., vol. 7 No. 5, Apr. 2016, pp. 319-334.
Schmidt S. T et al., "Liposome-Based Adjuvants for Subunit Vaccines: Formulation Strategies for Subunit Antigens and Immunostimulators" Pharmaceutics, Mar. 2016, vol. 8 No. 7, pp. 1-22.
Tyminski P. N. et al., "Rhodopsin in polymerized bilayer membranes" J. Am. Chem. Soc. vol. 107 No. 25, 1985, pp. 7769-7770.
Tyminski P. N. et al., "Reconstitution of Rhodopsin and the cGMP cascade in polymerized bilayer membranes" Biochemistry, vol. 27 No. 8, 1988, pp. 2696-2705.
Weissman D. et al., "mRNA transcript therapy" Expert Rev. Vaccines, 2014, pp. 1-17.

\* cited by examiner

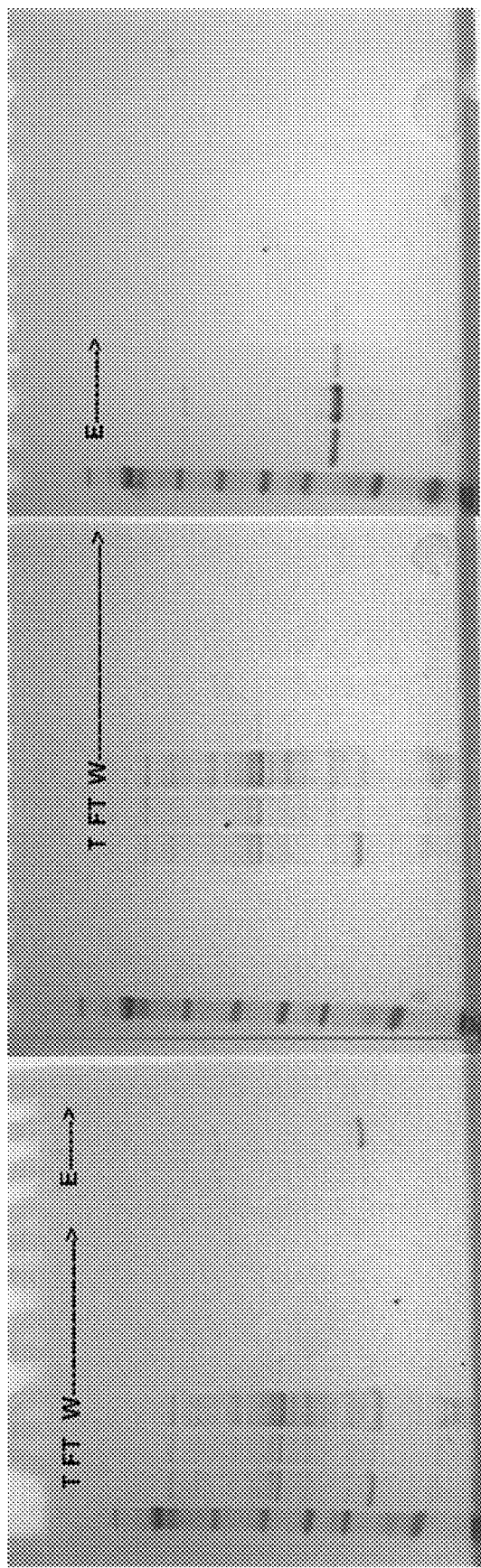
FIGURE 2A  NLP w/ DMPC
FIGURE 2B  Telo-

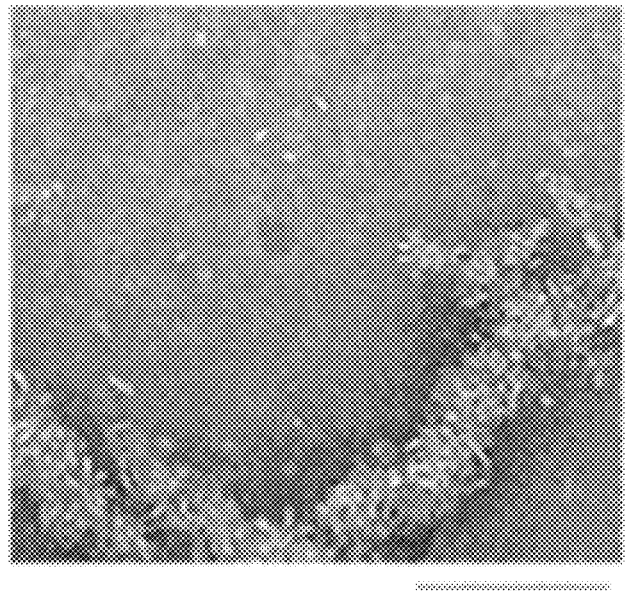
FIGURE 4A
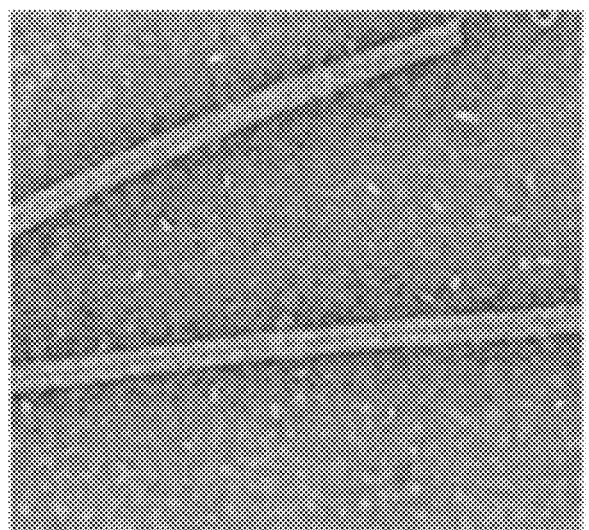 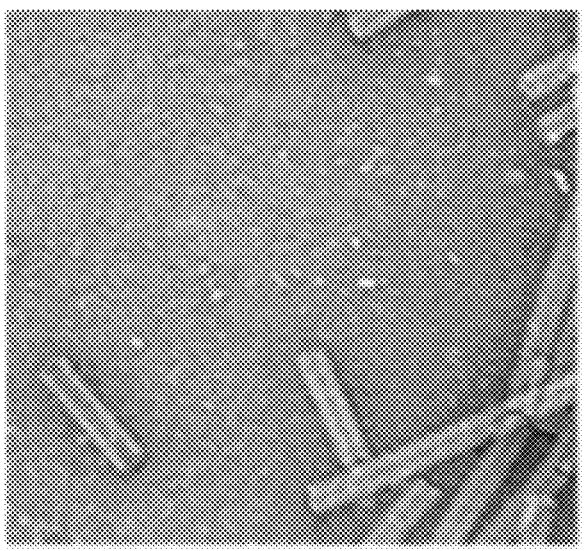
FIGURE 4B FIGURE 4C

SEQUENCE LISTING

<160> NUMBER OF SEQ ID NOS: 4

<210> SEQ ID NO 1
<211> LENGTH: 897
<212> TYPE: DNA
<213> ORGANISM: Homo sapiens
<220> FEATURE:
<221> NAME/KEY: misc_feature
<223> OTHER INFORMATION: human apolipoprotein A-1 (APOA1, apoAI, apoA-I)
      preproprotein cDNA

<400> SEQUENCE: 1
agagactgcg agaaggaggt ccccacggc ccttcaggat gaaagctgcg gtgctgacct      60
tggccgtgct cttcctgacg gggagccagg ctcggcattt ctggcagcaa gatgaacccc    120
cccagagccc ctgggatcga gtgaaggacc tggccactgt gtacgtggat gtgctcaaag    180
acagcggcag agactatgtg tcccagtttg aaggctccgc cttgggaaaa cagctaaacc    240
taaagctcct tgacaactgg gacagcgtga cctccacctt cagcaagctg cgcgaacagc    300
tcggccctgt gacccaggag ttctgggata acctggaaaa ggagacagag ggcctgaggc    360

```
aggagatgag caaggatctg gaggaggtga aggccaaggt gcagccctac ctggacgact    420
tccagaagaa gtggcaggag gagatggagc tctaccgcca gaaggtggag ccgctgcgcg    480
cagagctcca agagggcgcg cgccagaagc tgcacgagct gcaagagaag ctgagcccac    540
tgggcgagga gatgcgcgac cgcgcgcgcg cccatgtgga cgcgctgcgc acgcatctgg    600 cccctacag cgacgagctg cgccagcgct tggccgcgcg ccttgaggct ctcaaggaga    660
acggcggcgc cagactggcc gagtaccacg ccaaggccac cgagcatctg agcacgctca    720
gcgagaaggc caagcccgcg ctcgaggacc tccgccaagg cctgctgccc gtgctggaga    780
gcttcaaggt cagcttcctg agcgctctcg aggagtacac taagaagctc aacacccagt    840
gaggcgcccg ccgccgcccc ccttcccggt gctcagaata aacgtttcca aagtggg       897
```

```
<210> SEQ ID NO 2
<211> LENGTH: 715
<212> TYPE: DNA
<213> ORGANISM: Artificial Sequence
<220> FEATURE:
<223> OTHER INFORMATION: synthetic truncated apolipoprotein A-1,
      truncated delta49 apolipoprotein A-1, truncated form of Apo A1
      (delta49A1, delta1-49, delta49ApoA1, delta-ApoA1) cDNA

<400> SEQUENCE: 2
agcggcagag actatgtgtc ccagtttgaa ggctccgcct tgggaaaaca gctaaaccta     60
aagctccttg acaactggga cagcgtgacc tccaccttca gcaagctgcg cgaacagctc    120
ggccctgtga cccaggagtt ctgggataac ctggaaaagg agacagaggg cctgaggcag    180
gagatgagca aggatctgga ggaggtgaag gccaaggtgc agccctacct ggacgacttc    240
cagaagaagt ggcaggagga gatggagctc taccgccaga aggtggagcc gctgcgcgca    300
gagctccaag agggcgcgcg ccagaagctg cacgagctgc aagagaagct gagcccactg    360
ggcgaggaga tgcgcgaccg cgcgcgcgcc catgtggacg cgctgcgcac gcatctggcc    420
ccctacagcg acgagctgcg ccagcgcttg gccgcgcgcc ttgaggctct caaggagaac    480
ggcggcgcca gactggccga gtaccacgcc aaggccaccg agcatctgag cacgctcagc    540
gagaaggcca agcccgcgct cgaggacctc cgccaaggcc tgctgcccgt gctggagagc    600
ttcaaggtca gcttcctgag cgctctcgag gagtacacta agaagctcaa cacccagtga    660
ggcgcccgcc gccgcccccc ttcccggtgc tcagaataaa cgtttccaaa gtggg         715
```

```
<210> SEQ ID NO 3
<211> LENGTH: 267
<212> TYPE: PRT
<213> ORGANISM: Homo sapiens
<220> FEATURE:
<221> NAME/KEY: MISC_FEATURE
<223> OTHER INFORMATION: human apolipoprotein A-1 (APOA1, apoAI, apoA-I)
      preproprotein

<400> SEQUENCE: 3

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
```

```
                 65                  70                  75                  80
        Phe Ser Lys Leu Arg Glu Gln Leu Gly Pro Val Thr Gln Glu Phe Trp
                         85                  90                  95

Asp Asn Leu Glu Lys Glu Thr Glu Gly Leu Arg Gln Glu Met Ser Lys
                        100                 105                 110

Asp Leu Glu Glu Val Lys Ala Lys Val Gln Pro Tyr Leu Asp Asp Phe
                    115                 120                 125

Gln Lys Lys Trp Gln Glu Glu Met Glu Leu Tyr Arg Gln Lys Val Glu
                130                 135                 140

Pro Leu Arg Ala Glu Leu Gln Glu Gly Ala Arg Gln Lys Leu His Glu
        145                 150                 155                 160

Leu Gln Glu Lys Leu Ser Pro Leu Gly Glu Glu Met Arg Asp Arg Ala
                        165                 170                 175

Arg Ala His Val Asp Ala Leu Arg Thr His Leu Ala Pro Tyr Ser Asp
                    180                 185                 190

Glu Leu Arg Gln Arg Leu Ala Ala Arg Leu Glu Ala Leu Lys Glu Asn
                195                 200                 205

Gly Gly Ala Arg Leu Ala Glu Tyr His Ala Lys Ala Thr Glu His Leu
            210                 215                 220

Ser Thr Leu Ser Glu Lys Ala Lys Pro Ala Leu Glu Asp Leu Arg Gln
        225                 230                 235                 240

Gly Leu Leu Pro Val Leu Glu Ser Phe Lys Val Ser Phe Leu Ser Ala
                        245                 250                 255

Leu Glu Glu Tyr Thr Lys Lys Leu Asn Thr Gln
                        260                 265

<210> SEQ ID NO 4
<211> LENGTH: 219
<212> TYPE: PRT
<213> ORGANISM: Artificial Sequence
<220> FEATURE:
<223> OTHER INFORMATION: synthetic truncated human apolipoprotein A-1,
      truncated delta49, apolipoprotein A-1, truncated form of Apo A1
      (delta49A1, delta1-49, delta49ApoA1, delta-ApoA1)

<400> SEQUENCE: 4

Ser Gly Arg Asp Tyr Val Ser Gln Phe Glu Gly Ser Ala Leu Gly Lys
1               5                   10                  15

Gln Leu Asn Leu Lys Leu Leu Asp Asn Trp Asp Ser Val Thr Ser Thr
                20                  25                  30

Phe Ser Lys Leu Arg Glu Gln Leu Gly Pro Val Thr Gln Glu Phe Trp
            35                  40                  45

Asp Asn Leu Glu Lys Glu Thr Glu Gly Leu Arg Gln Glu Met Ser Lys
        50                  55                  60

Asp Leu Glu Glu Val Lys Ala Lys Val Gln Pro Tyr Leu Asp Asp Phe
65                  70                  75                  80

Gln Lys Lys Trp Gln Glu Glu Met Glu Leu Tyr Arg Gln Lys Val Glu
                85                  90                  95

Pro Leu Arg Ala Glu Leu Gln Glu Gly Ala Arg Gln Lys Leu His Glu
            100                 105                 110

Leu Gln Glu Lys Leu Ser Pro Leu Gly Glu Glu Met Arg Asp Arg Ala
        115                 120                 125

Arg Ala His Val Asp Ala Leu Arg Thr His Leu Ala Pro Tyr Ser Asp
    130                 135                 140

Glu Leu Arg Gln Arg Leu Ala Ala Arg Leu Glu Ala Leu Lys Glu Asn
145                 150                 155                 160
```

| | | | | | | | | | | | | |
|---|---|---|---|---|---|---|---|---|---|---|---|---|
| Gly | Gly | Ala | Arg | Leu | Ala | Glu | Tyr | His | Ala | Lys | Ala | Thr | Glu | His | Leu |
| | | | | 165 | | | | | 170 | | | | | 175 | |
| Ser | Thr | Leu | Ser | Glu | Lys | Ala | Lys | Pro | Ala | Leu | Glu | Asp | Leu | Arg | Gln |
| | | | 180 | | | | | 185 | | | | | 190 | | |
| Gly | Leu | Leu | Pro | Val | Leu | Glu | Ser | Phe | Lys | Val | Ser | Phe | Leu | Ser | Ala |
| | | 195 | | | | | 200 | | | | | 205 | | | |
| Leu | Glu | Glu | Tyr | Thr | Lys | Lys | Leu | Asn | Thr | Gln |
| | 210 | | | | | 215 | | | | |

APOLIPOPROTEIN NANODISCS WITH TELODENDRIMER

CROSS-REFERENCES TO RELATED APPLICATIONS

This application is a continuation of, and claims priority to U.S. patent application Ser. No. 15/499,855, filed on Apr. 27, 2017, and entitled "Apolipoprotein Nanodiscs with Telodendrimer," which in turn, is a continuation of, and claims priority to U.S. patent application Ser. No. 13/719, 785, filed Dec. 19, 2012, now U.S. Pat. No. 9,644,038, issued on May 9, 2017 and entitled "Apolipoprotein Nanodiscs with Telodendrimer," which in turn claims priority to U.S. Provisional Application Ser. No. 61/578,583, filed Dec. 21, 2011, and entitled "Apolipoprotein Nanodiscs with Telodendrimer," the content of each of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Grant No. R01CA115483, awarded by the National Institutes of Health and Contract No. DE-AC52-07NA27344 between the United States Department of Energy and Lawrence Livermore National Security, LLC, for the operation of Lawrence Livermore National Laboratory.

BACKGROUND OF THE INVENTION

NLPs are discoidal nanoparticles formed when apolipoproteins and a population of phospholipids self-assemble into nanometer-sized discs containing a bilayer that is fully soluble in an aqueous environment. Nanolipoprotein particles (NLPs) are nanoscale (6-30 nm), discoidal patches of lipid bilayer stabilized by peripheral scaffold. NLPs present distinct advantages over currently used membrane systems in terms of particle size and consistency: the presence of the circular apolipoprotein "belt" that constrains the dimensions of the bilayer and helps ensure discrete NLP particle sizes between preparations compared to current model membranes. The protein belt also makes NLPs more thermally stable over time compared to micelles and liposomes. This bilayer is thought to closely mimic the cell membrane, providing a hydrophobic patch for the incorporation of membrane proteins as well as a region for the interaction of drugs and other small molecules.

Currently, the greatest use of NLPs has been the stabilization and characterization of membrane proteins. Noteworthy, is the fact that these artificial lipid systems were more soluble with less sample heterogeneity compared to proteins prepared from microsomes. The combined use of cell-free-NLPs production allows for the soluble presentation of membrane proteins in a highly controlled environment. Cell-free systems also permit unique labeling/tagging strategies not readily available to whole cell systems and allows one to go from a gene to protein to structure in a single day. Cell-free systems can accommodate additives that augment protein expression; including: chaperonins, lipids, redox factors, and detergents and protease inhibitors. More recently GPCRs and model proteins such as bacteriorhodopsin, have been reconstituted into NLPs using DMPC alone, POPC alone or a mixture of POPC/POPG demonstrating that lipid effects can be used to fine tune NLP applications. Other additives that alter lipid:apoprotein interactions could aid in solubilization and NLPs. Importantly, this can all be accomplished in a single reaction, in a high-throughput manner for testing a variety of conditions to identify optimal functional parameters.

The development of several amphiphilic PEG-dendritic block copolymers (telodendrimers) was previously shown to have several favorable nanoproperties for both cancer imaging and therapy using micelles. The particles were 20-80 nm. This size is generally smaller than many of the reported nanoparticles and liposomes, containing a well-defined and easily fine-tuned PEG corona. Importantly the use of PEG could minimize the nonspecific binding as well as biological degradation in vivo. Although the micelles were designed for packaging drug and imaging agents buried inside the hydrophobic core the telodendrimers themselves provide convenient covalent attachment sites that could be used for presenting active targeting and cellular uptake molecules on the surface. The possibility of incorporating the telodendrimer functionality on a different nanoplatform such as the NLPs could aid in the development of a novel multifaceted nanoparticle capable of carrying therapeutic peptides with imaging functions displayed on the surface of the nanoparticles. Surprisingly, the present invention meets this and other needs.

BRIEF SUMMARY OF THE INVENTION

In one aspect, the present invention provides a nanodisc including a membrane scaffold protein, a telodendrimer and a lipid.

In a second aspect, the present invention provides a cell-free method of making a nanodisc. The method includes forming a vesicle having a telodendrimer and a lipid, wherein the ratio of lipid to telodendrimer is from about 500:1 to about 1:1 (w/w). The method also includes forming a reaction mixture of the vesicle and a membrane scaffold protein in the absence of a cell, thereby preparing the nanodisc.

BRIEF DESCRIPTION OF THE DRAWINGS

FIG. 1A.) The chemical structure of a telodendrimer comprised of an octamer of cholic acid (CA8) linked to the terminal end of a linear 5 kDa PEG molecule (PEGK), which is solubilized with DMPC lipid. FIG. 1B.) The telodendrimer-lipid mixture is then added to a general cell free reaction, resulting in the self-assembly of Telo-NLPs.

FIGS. 2A-2B show telodendrimer addition increase the yield and solubility of nanoparticles. A total of 1 ml cell-free expression reactions were run with and without Telodendrimer $PEG^{5K}$-$CA_8$ in DMPC. A typical comparison of the differing fractions produced throughout the purification is shown. The following symbols are T=total reaction, FT=flow through, W=wash and E=elution fractions. Elution fractions were centrifuged to remove non-soluble components. FIG. 2A shows a 4-12% SDS-PAGE gel for the purification profile of a NLP assembled with DMPC alone. FIG. 2B shows a 4-25% SDS-PAGE gel for the purification profile of a NLP assembled using DMPC and telodendrimer additives.

FIG. 3A, The size distribution of telodendrimer-NLPs measured by Dynamic Light Scattering. Telodendrimer-NLPs demonstrated an improved homogeneity compared to normal DMPC-NLP. FIG. 3B, Total aggregation of various telodendrimer-NLPs show significantly less aggregation compared to normal DMPC-NLP (p<0.01). FIG. 3C, PEG tail length and size of the telodendrimer-NLPs are significantly correlated (PEG$^{2K}$ vs PEG$^{5K}$, p<0.01).

FIGS. 4A-4D show disc-like structures with decreased aggregation of telodendrimer NLP complexes compared with NLP alone. CryoEM visualization of NLP preparations with and without telodendrimers are shown to reduce aggregation levels of Telo-NLPs. FIG. 4A: NLP assembly using DMPC lipids alone. FIG. 4B: NLP assembly using DMPC lipids with 10% telodendrimer PEG$^{2K}$-CA$_4$. FIG. 4C: NLP assembly using DMPC lipids with 10% telodendrimer PEG$^{2K}$-CA$_8$. FIG. 4D: Magnification of NLP with 10% PEG$^{GK}$-CA$_8$ (arrowhead) from it's top view. Tubular structures (white arrow) represent Tobacco Mosaic Viruses for reference.

FIG. 6A). The pictures of the tubes were taken after the reactions were finished. FIG. 6B). Denaturing SDS PAGE gel electrophoresis of cell-free expressed proteins. All samples were loaded along with a molecular weight standard (M.W.). The pictures were taken with GE-TYPHOON 9410 using laser/filter 488 nm/520 nm. The non-specific bands below 20 kDa are free BODIPY-FL. The tubes and lanes are as follows: 1. Coexpression of BR and ApoA1 with DMPC (BR-NLP), 2. Cell free expression of ApoA1 with DMPC (empty NLP), 3. Coexpression of BR and ApoA1 with DMPC and 0.5% telodendrimer PEG$^{2k}$-CA$_4$. 4. Coexpression of BR and ApoA1 with DMPC and 0.5% telodendrimer PEG$^{2k}$-CA$_8$. 5. Coexpression of BR and ApoA1 with DMPC and 0.5% telodendrimer PEG$^{5k}$-CF$_4$. 6. Coexpression of BR and ApoA1 with DMPC and 0.5% telodendrimer PEG$^{5k}$-CA$_8$.

DETAILED DESCRIPTION OF THE INVENTION

I. General

Figure 1A:
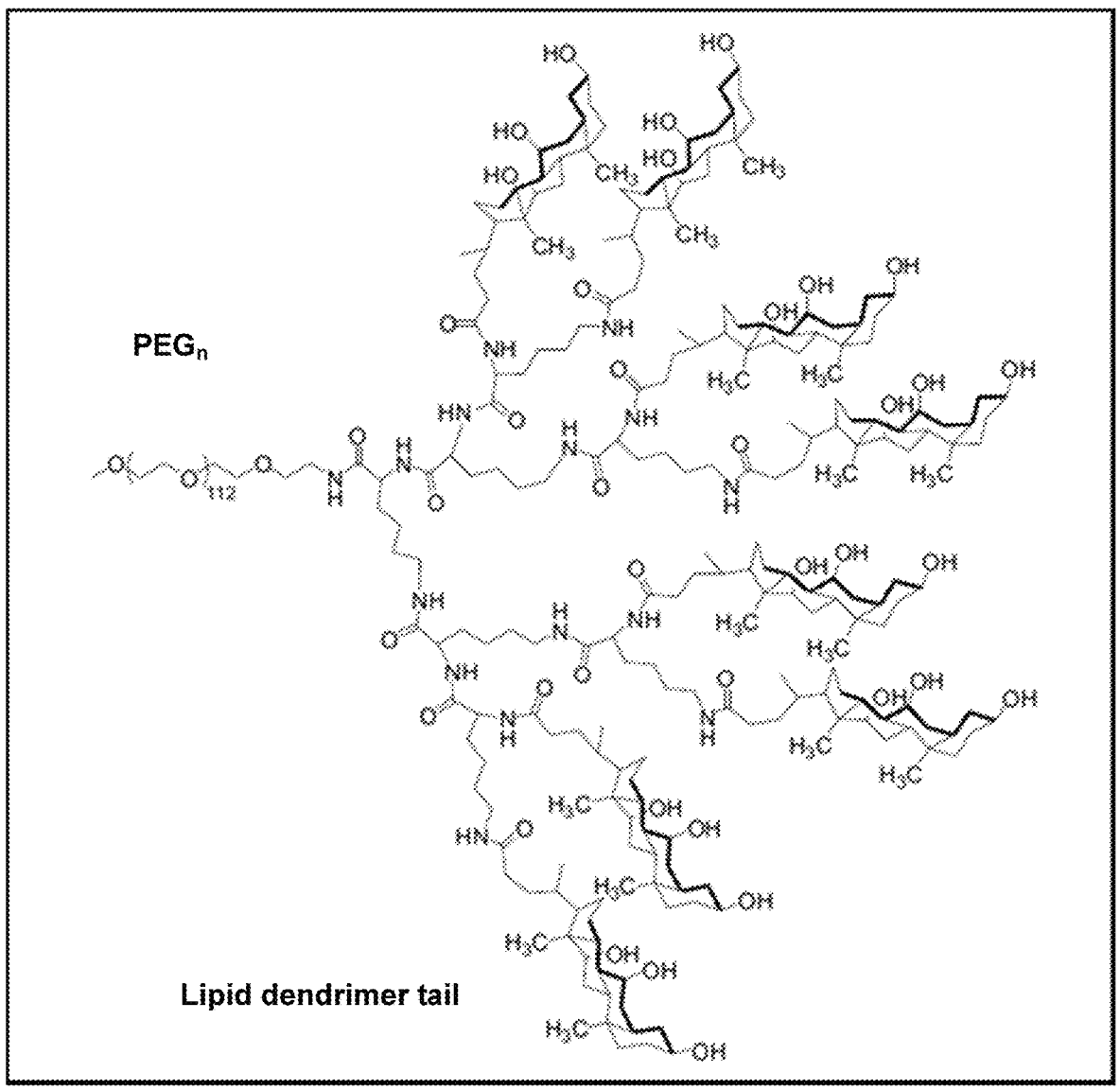
FIGS. 1A-1B show a schematic of cell-free synthesis of telodendrimer conjugated NLPs.

The present invention is based on the surprising discovery that amphiphilic polymer conjugates, called "elodendrimers," can bind and stabilize phospholipid bilayers to provide discrete nanostructures termed hybrid nanodiscs (hybrid-ND) in the presence of a membrane scaffold protein. The telodendrimers of the present invention are block copolymers having a linear poly(ethylene glycol) (PEG) segment and a dendritic hydrophobic segment or a dendritic amphiphilic segment. Telodendrimers can also have additional functional groups such as cholic acid groups and hydrophobic drugs covalently bound to the dendritic segment. The invention also provides convenient methods for nanodisc generation.

II. Definitions

As used herein, the term "nanodisc" refers to at least one phospholipid bilayer that is stabilized by a lipid-binding species and an apolipoprotein. The preferred lipid binding species is a telodendrimer as disclosed herein, although other lipid-binding species (including proteins and peptides) are known. The nanodiscs of the present invention are less than one micron in diameter. The nanodiscs can optionally contain additional lipid components, drugs, proteins that are not membrane scaffold proteins, diagnostic agents, and targeting agents.

As used herein, the term "membrane scaffold protein" refers to a protein that can stabilize a phospholipid bilayer in a nanodisc by binding to the bilayer periphery. In general, membrane scaffold proteins have hydrophobic faces that can associate with the nonpolar interior of a phospholipid bilayer and hydrophilic faces that favorably interact with a polar solvent such as an aqueous buffer. Membrane scaffold protein sequences may be naturally occurring, or may be engineered using recombinant techniques or constructed de nova. Naturally occurring membrane scaffold proteins include apolipoproteins, which are components of lipoproteins. Known classes of apolipoproteins include: A (including, for example, apo A-I and apo A-II), B, C, D, E, and H. The membrane scaffold proteins can be the full length protein, or a truncated version of the protein. Membrane scaffold protein is not intended to encompass various functional membrane proteins including, but not limited to, ion channels and other transmembrane receptors, porins, certain cell adhesion molecules, and electron transport proteins such as NADH dehydrogenase and ATP synthases.

As used herein, the term "telodendrimer" refers to a dendrimer containing a hydrophilic PEG segment and one or more chemical moieties covalently bonded to one or more end groups of the dendrimer. These moieties can include, but are not limited to, hydrophobic groups, hydrophilic groups, amphiphilic compounds, and drugs. Different moieties may be selectively installed at desired end groups using orthogonal protecting group strategies.

As used herein, the terms "dendrimer" and "dendritic polymer" refer to branched polymers containing a focal point, a plurality of branched monomer units, and a plurality of end groups. The monomers are linked together to form arms (or "dendrons") extending from the focal point and terminating at the end groups. The focal point of the dendritic polymer can be attached to other segments of the telodendrimers, and the end groups may be further functionalized with additional chemical moieties.

As used herein, the terms "monomer" and "monomer unit" refer to repeating units that make up the dendrons of the dendritic polymers of the invention. The monomers may be AB2-type monomers, where A and B are two different functional groups capable of reacting together such that the resulting polymer chain has a branch point where an A-B bond is formed. Exemplary monomers include a diamino carboxylic acid, a dihydroxy carboxylic acid and a hydroxyl amino carboxylic acid. Examples of diamino carboxylic acid groups of the present invention include, but are not limited to, 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present invention include, but are not limited to, glyceric acid, 2,4-dihydroxybutyric acid, and 2,2-bis(hydroxymethyl)propionic acid. Examples of hydroxyl amino carboxylic acids include, but are not limited to, serine and homoserine. One of skill in the art will appreciate that other monomer units are useful in the present invention.

As used herein, the term "amino acid" refers to a carboxylic acid bearing an amine functional group. Amino acids include the diamino carboxylic acids described above. Amino acids include naturally occurring α-amino acids, wherein the amine is bound to the carbon adjacent to the carbonyl carbon of the carboxylic acid. Examples of naturally occurring α-amino acids include, but are not limited to, L-aspartic acid, L-glutamic acid, L-histidine, L-lysine, and L-arginine. Amino acids may also include the D-enantiomers of naturally occurring α-amino acids, as well as R-amino acids and other non-naturally occurring amino acids.

As used herein, the term "lipid" refers to lipid molecules that can include fats, waxes, steroids, cholesterol, fat-soluble vitamins, monoglycerides, diglycerides, triglycerides, phospholipids, sphingolipids, glycolipids, cationic or anionic lipids, derivatized lipids, and the like, as described in detail below. Lipids can form micelles, monolayers, and bilayer membranes. The lipids can self-assemble in combination with other components to form nanodiscs.

As used herein, the term "hydrophobic group" refers to a chemical moiety that is water-insoluble or repelled by water. Examples of hydrophobic groups include, but are not limited to, long-chain alkanes and fatty acids, fluorocarbons, silicones, certain steroids such as cholesterol, and many polymers including, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as poly(ethylene glycol) (PEG).

As used herein, the term "amphiphilic compound" refers to a compound having both hydrophobic portions and hydrophilic portions. For example, the amphiphilic compounds of the present invention can have one hydrophilic face of the compound and one hydrophobic face of the compound. Amphiphilic compounds useful in the present invention include, but are not limited to, cholic acid and cholic acid analogs and derivatives, and cholesterol formate.

As used herein, the term "cholic acid" refers to (R)-4-((3R, 5S, 7R, 8R, 9S, 10S, 12S, 13R, 14S, 17R)-3,7,12-trihydroxy-10, 13-dimethylhexadecahydro-1H-cyclopenta[α]phenanthren-17-yl)pentanoic acid. Cholic acid is also known as 3α,7α,12α-trihydroxy-5β-cholanoic acid; 3-α,7-α,12-α-Trihydroxy-5-β-cholan-24-oic acid; 17-β-(1-methyl-3-carboxypropyl)etiocholane-3α,7α,12 α-triol; cholalic acid; and cholalin. Cholic acid derivatives and analogs, such as allocholic acid, pythocholic acid, avicholic acid, deoxycholic acid, and chenodeoxycholic acid are also useful in the present invention. Cholic acid derivatives can be designed to modulate the properties of the nanodiscs resulting from telodendrimer assembly, such as stability and membrane activity. For example, the cholic acid derivatives can have hydrophilic faces that are modified with one or more glycerol groups, aminopropanediol groups, or other groups.

As used herein, the terms "drug" or "therapeutic agent" refers to an agent capable of treating and/or ameliorating a condition or disease. Drugs useful in the present invention include, but are not limited to, paclitaxel, doxorubicin, etoposide, irinotecan, SN-38, cyclosporin A, podophyllotoxin, Carmustine, Amphotericin B, Ixabepilone, Patupilone (epothelone class), rapamycin and platinum drugs. The drugs of the present invention also include prodrug forms. One of skill in the art will appreciate that other drugs are useful in the present invention.

As used herein, "forming a reaction mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

As used herein, the term "solvent mixture" refers to a mixture of two or more solvents selected for suspension and/or dissolution of nanodisc components in a reaction mixture. The solvents in the mixture and the volume ratio in which they are combined depend primarily on the polarity of the lipids and telodendrimers in the reaction mixture. Non-limiting examples of solvents for use in the solvent mixture include chloroform, dichloromethane, ethanol, methanol, acetone, hexanes, petroleum ether, diethyl ether, dioxane, tetrahydrofuran, and water.

As used herein, the term "lysate" refers to the products produced after breaking down a cell.

As used herein, the term "buffer" refers to an aqueous solution capable of maintaining the pH of the solution at a nearly constant value. The buffer accomplishes this by including a weak acid and its conjugate base, such that the pH does not substantially change following addition of a small amount of acid or base. Representative buffering agents include citric acid, acetic acid, dipotassium phosphate ($K_2HPO_4^-$), N-cyclohexyl-2-aminoethanesulfonic acid (CHES), and borate. Buffers commonly used include, but are not limited to, TAPS, bicine, tris, tricine, TAPSO, HEPES, TES, MOPS, PIPES, cacodylate, SSC, MES and succinic acid.

As used herein, the term "polymerase" refers to an enzyme capable of synthesizing nucleic acid polymers. The polymerase can be a DNA or an RNA polymerase. Representative polymerases include DNA polymerase I, DNA polymerase II, DNA polymerase III holoenzyme, DNA polymerase IV, RNA polymerase I, RNA polymerase II, RNA polymerase III and T7 RNA polymerase. Other polymerases are useful in the present invention.

III. Telodendrimers

Telodendrimers useful in the present invention include any telodendrimer having a polyethyleneglycol (PEG) polymer linked to a dendrimer functionalized with a hydrophobic group, a hydrophilic group, an amphiphilic compound or a drug on the dendrimer periphery. In some embodiments, the invention provides a compound of formula I:

$$PEG\text{-}D\text{-}(R)n \quad (I)$$

wherein radical D of formula I is a dendritic polymer having a single focal point group, a plurality of branched monomer units X and a plurality of end groups. PEG of formula I is a polyethyleneglycol (PEG) polymer, wherein each PEG polymer has a molecular weight of 1-100 kDa. Each R of formula I is independently the end group of the dendritic polymer or an amphiphilic compound, such that when R is not an end group each R is linked to one of the end groups. Subscript n of formula I is an integer from 2 to 20, wherein subscript n is equal to the number of end groups on the dendritic polymer, and wherein at least half the number n of R groups are each an amphiphilic compound.

The dendritic polymer can be any suitable dendritic polymer. The dendritic polymer can be made of branched monomer units including amino acids or other bifunctional AB2-type monomers, where A and B are two different functional groups capable of reacting together such that the resulting polymer chain has a branch point where an A-B bond is formed. In some embodiments, each branched monomer unit X can be a diamino carboxylic acid, a dihydroxy carboxylic acid and a hydroxyl amino carboxylic acid. In some embodiments, each diamino carboxylic acid can be 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-mnethyl propanoic acid, 4-amino-2-(2-aminoethyl) butyric acid or 5-amino-2-(3-aminopropyl) pentanoic acid. In some embodiments, each dihydroxy carboxylic acid can be glyceric acid, 2,4-dihydroxybutyric acid, 2,2-Bis(hydroxymethyl)propionic acid, 2,2-Bis(hydroxymethyl)butyric acid, serine or threonine. In some embodiments, each hydroxyl amino carboxylic acid can be serine or homoserine. In some embodiments, the diamino carboxylic acid is an amino acid. In some embodiments, each branched monomer unit X is lysine. In some embodiments, the dendritic polymer can be a poly(lysine) dendritic polymer wherein each end group can be hydroxy.

The focal point of a telodendrimer or a telodendrimer segment may be any suitable functional group. In some embodiments, the focal point includes a functional group that allows for attachment of the telodendrimer or telodendrimer segment to another segment. The focal point functional group can be a nucleophilic group including, but not limited to, an alcohol, an amine, a thiol, or a hydrazine. The focal point functional group can also be an electrophile such as an aldehyde, a carboxylic acid, or a carboxylic acid derivative including an acid chloride or an N-hydroxysuccinimidyl ester.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

The telodendrimer backbone can vary, depending on the number of branches and the number and chemical nature of the end groups and R groups, which will modulate solution conformation, rheological properties, and other characteristics. The telodendrimers can have any suitable number n of end groups and any suitable number of R groups. In some embodiments, n can be 2-70, or 2-50, or 2-30, or 2-10. In some embodiment, n is 2-20.

The R groups installed at the telodendrimer periphery can be any suitable chemical moiety, including hydrophilic groups, hydrophobic groups, or amphiphilic compounds. Examples of hydrophobic groups include, but are not limited to, long-chain alkanes and fatty acids, fluorocarbons, silicones, certain steroids such as cholesterol, and many polymers including, for example, polystyrene and polyisoprene. Examples of hydrophilic groups include, but are not limited to, alcohols, short-chain carboxylic acids, amines, sulfonates, phosphates, sugars, and certain polymers such as PEG. Examples of amphiphilic compounds include, but are not limited to, molecules that have one hydrophilic face and one hydrophobic face.

Amphiphilic compounds useful in the present invention include, but are not limited to, cholic acid and cholic acid analogs and derivatives. "Cholic acid" refers to (R)-4-((3R, 5S, 7R, 8R, 9S, 10S, 12S, 13R, 14S 17R)-3,7,12-trihydroxy-10,13-dimethylhexadecahydro-1H-cyclopenta[α]phenanthren-17-yl)pentanoic acid, having the structure:

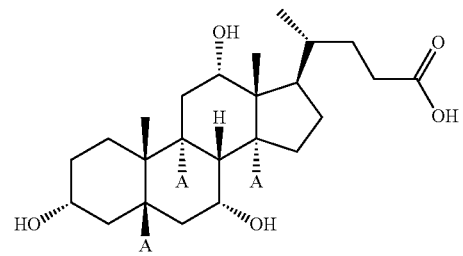

Cholic acid derivatives and analogs include, but are not limited to, allocholic acid, pythocholic acid, avicholic acid, deoxycholic acid, and chenodeoxycholic acid. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

In some embodiments, each R can be cholic acid, (3α, 5β, 7α, 12α)-7,12-dihydroxy-3-(2,3-dihydroxy-1-propoxy)-cholic acid, (3α, 5β,7α, 12α)-7-hydroxy-3,12-di(2,3-dihydroxy-1-propoxy)-cholic acid, (3α, 5β, 7α, 12a)-7,12-dihydroxy-3-(3-amino-2-hydroxy-1-propoxy)-cholic acid, cholesterol formate (CF), doxorubicin, or rhein. In some embodiments, each amphiphilic compound is cholic acid (CA). In some embodiments, each amphiphilic compound is cholesterol formate (CF).

Telodendrimer end groups can also include drugs such as paclitaxel, doxorubicin, etoposide, irinotecan, SN-38, cyclosporin A, podophyllotoxin, carmustine, amphotericin, ixabepilone, patupilone (epothelone class), rapamycin and platinum drugs. One of skill in the art will appreciate that other drugs are useful in the present invention.

The telodendrimer can have a single type of R group on the periphery, or any combination of R groups in any suitable ratio. In general, at least half the number n of R groups are other than an end group. For example, at least half the number n of R groups can be a hydrophobic group, a hydrophilic group, an amphiphilic compound, a drug, or any combination thereof. In some embodiments, half the number n of R groups are amphiphilic compounds.

In some embodiments, all the R groups are an amphiphilic group such as cholic acid or cholesterol formate. In other embodiments, some of the R groups are an end group of the dendrimer. In some other embodiments, at least two different R groups are present, such as two different amphiphilic groups, or an amphiphilic group and a drug, or an amphiphilic group and a dendritic polymer end group, or two different drugs, or a drug and a dendritic end group.

Telodendrimers useful in the present invention include, but are not limited to, $PEG^{2K}$-D-$CA_4$, $PEG^{5K}$-D-$CA_4$, $PEG^{10K}$-D-$CA_4$, $PEG^{2K}$-D-$CA_8$, $PEG^{5K}$-D-$CA_8$, $PEG^{10K}$-D-$CA_8$, $PEG^{2K}$-D-$CF_4$, $PEG^{5K}$-D-$CF_4$, $PEG^{10K}$-D-$CF_4$, $PEG^{2K}$-D-$CF_8$, $PEG^{5K}$-D-$CF_8$, or $PEG^{10K}$-D-$CF_8$, wherein each dendritic polymer D is a poly(lysine) dendritic polymer wherein each end group is hydroxy. In some embodiments, the telodendrimer can be $PEG^{2K}$-D-$CA_4$, $PEG^{2K}$-D-$CA_8$, $PEG^{5K}$-D-$CA_8$, $PEG^{5K}$-D-$CF_4$, $PEG^{10K}$-D-$CF_4$, or $PEG^{5K}$-D-$CF_8$. In some embodiments, the telodendrimer can be $PEG^{5K}$-D-$CA_8$, $PEG^{5K}$-D-$CA_4$ or $PEG^{2K}$-D-$CA_4$.

In some embodiments, the telodendrimer can have any of the following formulas:

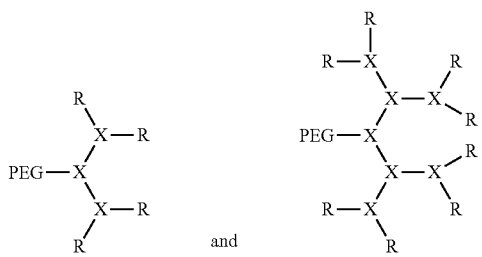

wherein each monomer unit X is lysine.

The telodendrimers useful in the present invention are known and can be prepared by a variety of methods, such as those described in PCT Publication No. WO 2010/039496.

IV. Nanodiscs

As described above, apolipoprotein-containing nanodisc drug formulations have shown in vitro and in vivo activity, but demonstrate limited stability and suffer from the drawbacks associated with the use of recombinant proteins. Telodendrimers offer several advantages when used in combination with recombinant apolipoprotein and incorporated into the lipid nanodisc formulations. Telodendrimers are synthetic polymers and easy to scale up. The telodendrimer components (namely PEG and biomolecules including lysine and cholic acid), the telodendrimers, and the telodendrimer-containing nanodiscs are fully biocompatible. The telodendrimer PEG component, presented on the nanodisc surface, reduces particle aggregation due to stacking of the lipid nanodisc. PEGylation can also prevent the rapid clearance of nanodiscs by the reticuloendothelial system, thus providing a sustained delivery of drug to a target site. In addition, the multifunctional telodendrimers allow for the introduction of targeting molecules for specific delivery of drugs to targeted cells, tissues, tumors, or microorganisms. Furthermore, the size and drug loading capacity of the hybrid-ND can easily be tuned by varying the configuration of the telodendrimers, the use of different telodendrimer-lipid combinations or adjusting the ratio of lipid-to-telodendrimer in the final pharmaceutical formulation.

In one aspect, the present invention provides a nanodisc with a membrane scaffold protein. The nanodisc includes a membrane scaffold protein, a telodendrimer and a lipid.

Any suitable membrane scaffold protein can be used in the nanodiscs of the present invention. Representative membrane scaffold proteins include, but are not limited to, apolipoproteins A (including, for example, apo A-1 and apo A-2), B, C, D, E, and H. In some embodiments, the membrane scaffold protein can be apolipoprotein. In some embodiments, the membrane scaffold protein can be apolipoprotein A-1. The membrane scaffold protein can be the full length protein, or a truncated version of the full length portion. In some embodiments, the membrane scaffold protein can be the truncated apolipoprotein A-1 (Δ49A1).

The telodendrimers that are useful in the present invention are described above and are amphiphilic conjugates having a hydrophilic PEG segment and an amphiphilic or hydrophobic segment. The amphiphilic segment of the telodendrimer can contain cholic acid, or other suitable amphiphilic moiety, which has a hydrophobic face and a hydrophilic face. The cholic acid and the PEG are connected by dendritic polymers that can contain a variety of acid repeats units. Typically, the dendritic polymers include a diamino carboxylic acid such as lysine.

The nanodiscs of the present invention can contain any suitable lipid, including cationic lipids, zwitterionic lipids, neutral lipids, or anionic lipids. Suitable lipids can include fats, waxes, steroids, cholesterol, fat-soluble vitamins, monoglycerides, diglycerides, phospholipids, sphingolipids, glycolipids, cationic or anionic lipids, derivatized lipids, and the like. In some embodiments, the nanodisc contains a lipid selected from a phospholipid, a lysolipid, cholesterol, a phosphatidylcholine, a phosphatidylethanolamine, a phosphatidylglycerol, a phosphatidylserine, a phosphatidylinositol and a PEGylated lipid.

Suitable phospholipids include but are not limited to phosphatidylcholine (PC), phosphatidic acid (PA), phosphatidylethanolamine (PE), phosphatidylglycerol (PG), phosphatidylserine (PS), and phosphatidylinositol (PI), dimyristoyl phosphatidyl choline (DMPC), distearoyl phosphatidyl choline (DSPC), dioleoyl phosphatidyl choline (DOPC), dipalmitoyl phosphatidyl choline (DPPC), dimyristoyl phosphatidyl glycerol (DMPG), distearoyl phosphatidyl glycerol (DSPG), dioleoyl phosphatidyl glycerol (DOPG), dipalmitoyl phosphatidyl glycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), 1,2-dielaidoyl-sn-glycero-3-phophoethanolamine (transDOPE), and cardiolipin. Phospholipids can be lysolipids, which contain only one fatty acid moiety bonded to the glycerol subunit via an ester linkage. Lipid extracts, such as egg PC, heart extract, brain extract, liver extract, and soy PC, are also useful in the present invention. The lipids can include derivatized lipids, such as PEGylated lipids. Derivatized lipids can include, for example, DSPE-PEG2000, cholesterol-PEG2000, DSPE-polyglycerol, or other derivatives generally known in the art.

Nanodiscs of the present invention can contain steroids, characterized by the presence of a fused, tetracyclic nonane ring system. Examples of steroids include, but are not limited to, cholesterol, cholic acid, progesterone, cortisone, aldosterone, estradiol, testosterone, and dehydroepiandrosterone. Synthetic steroids and derivatives thereof are also contemplated for use in the present invention.

The nanodiscs can contain cationic lipids, which contain positively charged functional groups under physiological conditions. Cationic lipids include, but are not limited to, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N-[1-(2,3,-ditetradecyloxy)propyl]-N,N-dimethyl-N-hydroxyethylammonium bromide (DMRIE), N-[1-(2,3,dioleyloxy)propyl]-N,N-dimethyl-N-hydroxy ethylammonium bromide (DORIE), 3β-[N-(N,N'-dimethylaminoethane) carbamoyl]cholesterol (DC-Chol), dimethyldioctadecylammonium (DDAB) and N,N-dimethyl-2,3-dioleyloxy)propylamine (DODMA).

In some embodiments, the nanodisc of the present invention includes a lipid selected from 1,2-dipalmitoyl-sn-glycero-3-phosphocholine (DPPC), 1,2-ditetradecanoyl-sn-glycero-3-phosphocholine (DMPC), 1-tetradecanoyl-2-hexadecanoyl-sn-glycero-3-phosphocholine (MPPC), 1,2-dioctadecanoyl-sn-glycero-3-phosphocholine (DSPC), 1,2-distearoyl-sn-glycero-3-phosphoethanolamine (DSPE), 1,2-dihexadecanoyl-sn-glycero-3-phosphoethanolamine (DPPE), 1,2-distearoyl-sn-glycero-3-phospho-(1'-rac-glycerol) (DSPG), 1,2-dipalmitoyl-sn-glycero-3-phospho-(1'-rac-glycerol) (DPPG), 1-tetradecanoyl-2-hexadecanoyl-sn-glycero-3-phosphoglycerol (MPPG) and cholesterol. In some embodiments, the nanodisc contains a lipid of DMPC.

Any suitable combination of lipids can be used to provide the nanodiscs of the invention. The lipid compositions can be tailored to affect characteristics such as leakage rates, stability, particle size, zeta potential, protein binding, in vivo circulation, and/or accumulation in tissues or organs. For example, negative or positive lipids, such as DSPG and/or DOTAP, can be included to affect the surface charge of a nanodisc. The lipid compositions can include about ten or fewer types of lipids, or about five or fewer types of lipids, or about three or fewer types of lipids. In some embodiments, the lipid includes at least two different lipids. The molar percentage (mol %) of a specific type of lipid present can be from about 0% to about 10%, from about 10% to about 30%, from about 30% to about 50%, from about 50% to about 70%, from about 70% to about 90%, or from about 90% to 100% of the total lipid present in a nanodisc.

The nanodiscs of the invention may contain any suitable combination of lipids with telodendrimers and/or other components. The ratio of lipid to telodendrimer in the nanodisc, for example, can be from about 500:1 to about 1:1 (w/w). For example, the ratio can be about 500:1, 400:1, 300:1, 200:1, 100:1, 99:1, 95:1, 90:1, 80:1, 75:1, 70:1, 60:1, 50:1, 40:1, 30:1, 25:1, 20:1, 15:1, 14:1, 13:1, 12:1, 10:1, 9:1, 8:1, 7:1, 6:1, 5:1, 4:1, 3:1, 2:1 or 1:1 (w/w). In some embodiments, the ratio of lipid to telodendrimer is from about 200:1 to about 5:1 (w/w). In some embodiments, the ratio of lipid to telodendrimer is about 99:1 (w/w). In some embodiments, the ratio of lipid to telodendrimer is about 9:1 (w/w). Other weight ratios of lipid to telodendrimer can also be useful in the present invention.

In some embodiments, any of the nanodiscs as described above further include a drug. The drug can be noncovalently sequestered in the nanodisc, covalently linked to a telodendrimer conjugate as an R group as described above, covalently linked to the head group of the lipid, or otherwise associated with the nanodisc. Non-limiting examples of drugs that can be included in the nanodiscs are bortezomib, paclitaxel, SN38, camptothecin, etoposide and doxorubicin, docetaxel, daunorubicin, prednisone, dexamethasone, vincristine, vinblastine, temsirolimus and carmustine. Other suitable drugs include, but are not limited to, cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11) or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; cytarabine (ara-C), doxorubicin, cyclophosphamide, and gemcitabine. Other drugs useful in the nanocarrier of the present invention include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovorin, oxaliplatin (ELOXATIN™ from Sanofi-Synthelabo Pharmaceuticals, France), Pentostatin, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Raloxifene, Droloxafine, or Hexamethylmelamine. Prodrug forms are also useful in the present invention. Other drugs useful in the present invention also include radionuclides, such as $^{67}$C, $^{90}$Y, $^{123}$I, $^{125}$I, $^{131}$I, $^{177}$Lu, $^{18}$Re, $^{186}$Re and $^{211}$At. In some embodiments, the nanodiscs of the present invention include a drug selected from amphotericin B and SN38.

The nanodiscs can also include additional components such as diagnostic agents. A diagnostic agent used in the present invention can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal that includes, but is not limited to, gamma-emitting, radioactive, echogenic, optical, fluorescent, absorptive, magnetic or tomography signals. Techniques for imaging the diagnostic agent can also include single photon emission computed tomography (SPECT), magnetic resonance imaging (MRI), optical imaging, positron emission tomography (PET), computed tomography (CT), x-ray imaging, gamma ray imaging, and the like. A diagnostic agent can include chelators that bind to metal ions to be used for a variety of diagnostic imaging techniques. A radioisotope can be incorporated into some of the diagnostic agents described herein and can include radionuclides that emit gamma rays, positrons, beta and alpha particles, and X-rays. The diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). The diagnostic agents can include magnetic resonance (MR) and x-ray contrast agents that are known in the art, including, for example, iodine-based x-ray contrast agents, superparamagnetic iron oxide (SPIO), complexes of gadolinium or manganese, and the like. (See, e.g., Armstrong et al., *Diagnostic Imaging*. $5^{th}$ Ed., Blackwell Publishing (2004)). The diagnostic agents can be associated with the nanodiscs in a variety of ways including, for example, being covalently bound to a nanodisc component or noncovalently embedded or encapsulated in the nanodisc.

The nanodiscs can also include one or more targeting agents. Generally, a targeting agent can associate with any target of interest, such as a target associated with an organ, tissues, cell, extracellular matrix, or intracellular region. A target can be associated with a particular disease state, such as a cancerous condition. The targeting component can be specific to only one target, such as a receptor. Suitable targets can include but are not limited to a nucleic acid, such as a DNA, RNA, or modified derivatives thereof. Suitable targets can also include but are not limited to a protein, such as an extracellular protein, a receptor, a cell surface receptor, a tumor-marker, a transmembrane protein, an enzyme, or an antibody. The target can also be a carbohydrate, such as a monosaccharide, disaccharide, or polysaccharide that can be, for example, present on the surface of a cell. The targeting agent can be a target ligand (e.g., an RGD-containing peptide), a small molecule mimic of a target ligand (e.g., a peptide mimetic ligand), or an antibody or antibody fragment specific for a particular target. Targeting agents can further include folic acid derivatives, B-12 derivatives, NGR derivatives, somatostatin derivatives or peptides that bind to the somatostatin receptor, e.g., octreotide and octreotate, and the like. The targeting agents can also include an aptamer. Aptamers can be designed to associate with or bind to a target of interest. Aptamers can be comprised of, for example, DNA, RNA, and/or peptides, and certain aspects of aptamers are well known in the art. (See. e.g., Klussman, S., Ed., The Aptamer Handbook, Wiley-VCR (2006); Nissenbaum, E. T., *Trends in Biotech.* 26(8): 442-449 (2008)). The targeting agents can be associated with the nanodiscs in a variety of ways including, for example, being covalently bound to a nanodisc component or noncovalently embedded or encapsulated in the nanodisc. In particular, pathogen-, tissue-, or tumor-specific ligands can be covalently conjugated to the distal end of the PEG segment in the telodendrimer during synthesis to allow for targeted drug delivery.

Any measuring technique available in the art can be used to determine properties of the nanodiscs. For example, techniques such as dynamic light scattering, x-ray photoelectron microscopy, powder x-ray diffraction, scanning electron microscopy (SEM), transmission electron microscopy (TEM), and atomic force microscopy (AFM) can be used to determine average size and dispersity of the nanodiscs. In general, the nanodiscs of the present invention are less than one micron in diameter. The diameter of the nanodiscs can be from about 25 nm to about 900 nm in diameter, or from about 50 nm to about 750 nm in diameter, or from about 100 nm to about 500 nm in diameter. In some embodiments, the nanodisc is less than about 1000 nm in diameter. In some embodiments, the nanodisc is less that about 100 nm in diameter. In some embodiments, the nanodisc is less that about 10 nm in diameter. The diameter of the nanodisc may also be less than 900 nm, or less than 800 nm, or less than 700 nm, or less than 500 nm, or less than 400 nm, or less than 300 nm, or less than 200 nm, or less than 75 nm, or less than 50 nm, or less than 40 nm, or less than 30 nm, or less than 20 nm, or less than 10 nm.

V. Methods of Making Nanodiscs

The apolipoprotein-telodendrimer nanodiscs of the present invention can be prepared by any methods known in the art. These methods can be cell-based methods or cell-free methods, and generally involve forming a vesicle of the telodendrimer and lipid, followed by addition of a membrane scaffold protein, such as apolipoprotein, to form the nanodiscs of the present invention. In some embodiments, the method is a cell-free method.

In some embodiments, the present invention provides a cell-free method of making a nanodisc. The method includes forming a vesicle having a telodendrimer and a lipid, wherein the ratio of lipid to telodendrimer is from about 500:1 to about 1:1 (w/w). The method also includes forming a reaction mixture of the vesicle and a membrane scaffold protein in the absence of a cell, thereby preparing the nanodisc.

Figure 1B:
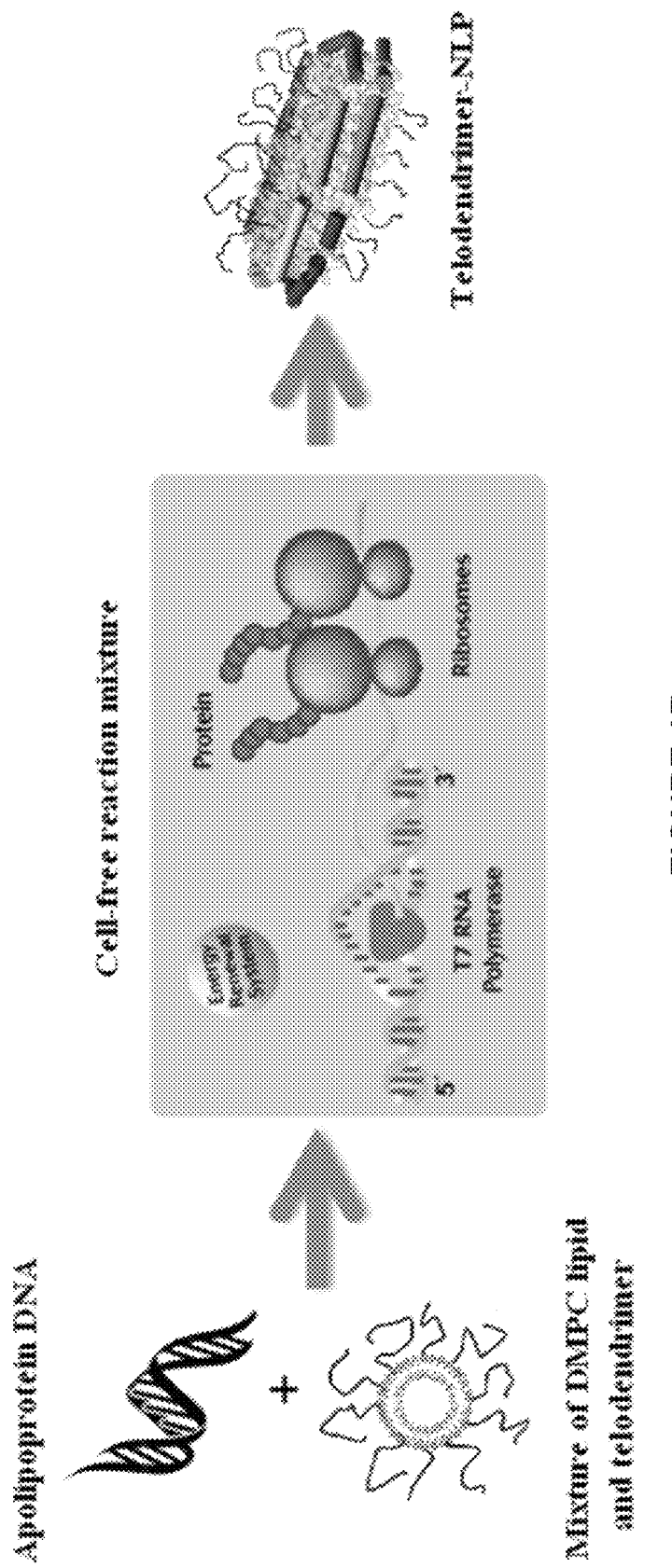

The cell-free process to produce NLPs in the presence of additional additives is outlined in FIGS. 1A-1B. Plasmid and telodendrimers were premixed with DMPC lipids, and added directly to cell free reactions to produce fully assembled nanoparticles. The NLPs were then separated with affinity purification. The entire process was completed in 4-24 hours and depended on the desired yield of total protein. Other additives such as fluorescent dyes used for visualization or membrane proteins/receptors encoded on plasmids were also included in some reactions.

Any membrane scaffold protein is suitable in the methods of the present invention. Representative membrane scaffold proteins are described above, and include, but are not limited to, apolipoprotein. In some embodiments, the membrane scaffold protein is apolipoprotein. In some embodiments, the apolipoprotein is apolipoprotein-A1. In some embodiments, the membrane scaffold protein can be the truncated apolipoprotein A-1 (Δ49A1).

Other optional components include lysates, buffers and polymerases. Any suitable lysate can be used, such as that provided by Santa Cruz Biotechnology. The reaction mixture can also include any suitable buffer, such as the Reaction Buffer, or PBS buffer. Suitable buffers include, but are not limited to, citric acid, acetic acid, dipotassium phosphate ($K_2HPO_4$). N-cyclohexyl-2-aminoethanesulfonic acid (CHES), borate, TAPS, bicine, tris, tricine, TAPSO, HEPES, TES, MOPS, PIPES, cacodylate, SSC, MES and succinic acid.

The reaction mixture can also include any suitable polymerase. Representative polymerases are described above. In some embodiments, the polymerase can be an RNA polymerase. The RNA polymerase can be suitable for preparing RNA from a DNA sequence, such as the apolipoprotein DNA sequence. In some embodiments, the polymerase can be RNA polymerase I, RNA polymerase II, RNA polymerase III or T7 RNA polymerase.

The nanodiscs of the invention can be prepared using any suitable ratio of lipid to telodendrimer. The ratio of lipid to telodendrimer in the nanodisc, for example, can be from about 500:1 to about 1:1 (w/w). For example, the ratio can be about 500:1, 400:1, 300:1, 200:1, 100:1, 99:1, 95:1, 90:1, 80:1, 75:1, 70:1, 60:1, 50:1, 40:1, 30:1, 25:1, 20:1, 15:1, 14:1, 13:1, 12:1, 10:1, 9:1, 8:1, 7:1, 6:1, 5:1, 4:1, 3:1, 2:1 or 1:1 (w/w). In some embodiments, the ratio of lipid to telodendrimer is from about 200:1 to about 5:1 (w/w). In some embodiments, the ratio of lipid to telodendrimer is about 99:1 (w/w). In some embodiments, the ratio of lipid to telodendrimer is about 9:1 (w/w). Other weight ratios of lipid to telodendrimer can also be useful in the present invention.

Any other suitable combination of lipids with telodendrimers and/or other components, as described above, can also be employed in the methods of the present invention. Still other weight ratios of lipid to telodendrimer may also be useful in the methods of the present invention. The methods may further include incorporation of additional components, such as drugs, diagnostic agents, and targeting agents, as described above, into the reaction mixture.

The reaction mixture generally includes a solvent or a mixture of solvents. In some embodiments, the reaction mixture further includes a solvent mixture. In general, the solvent mixture contains two or more solvents selected to sufficiently solubilize the lipid component and the telodendrimer component of the reaction mixture as well as any additional components. Suitable solvents include, but are not limited to, chloroform, dichloromethane, ethanol, methanol, acetone, hexanes, petroleum ether, diethyl ether, dioxane, tetrahydrofuran, and water.

In some embodiments, the method further includes contacting the dispersed lipid-telodendrimer mixture with a drug such that the drug is loaded into the nanodisc. The drug can be included in the solvent prior to contacting the lyophilized reaction mixture, or the drug may be added to the dispersed lipid-telodendrimer mixture after dispersion with the solvent. The dispersed lipid-telodendrimer mixture may be contacted with the drug for any amount of time sufficient to load the drug into the nanodiscs. So-called "passive" loading techniques involve the incorporation of drugs into a nanodisc during the nanodisc self-assembly process in solution, such that the drug is encapsulated or embedded within the nanodisc. Alternatively, the drugs can be actively loaded into nanodiscs. For example, the nanodiscs can be exposed to conditions, such as electroporation, in which the bilayer membrane is made permeable to a solution containing therapeutic agent thereby allowing for the drug to enter into the nanodisc. Loading of the nanodiscs with drugs or other components can be carried out via other methods known in the art, as disclosed for example in the following references: de Villiers, M. M. et al., Eds., *Nanotechnology in Drug Delivery*. Springer (2009); Gregoriadis, G., Ed., *Liposome Technology: Entrapment of drugs and other materials into liposomes*, CRC Press (2006).

The methods of the invention may optionally include additional steps such as sonication and/or freeze-thaw cycles to aid in dispersion and self-assembly, extrusion to yield nanodiscs with homogenous size and shape, dialysis to remove or exchange soluble species such as unbound drugs and buffer salts, and other steps. These optional steps may occur at any time during the methods of the invention.

VI. Examples

Example 1: Preparation of Nanodiscs with Apoliprotein and Telodendrimers

Methods

Plasmids: The truncated form of Apo A1 (Δ1-49) or Δ49ApoA1 was cloned into pIVEX2.4d using NdeI and SmaI restriction sites. This vector contained a His-tag used for nickel affinity purification as previously described (Cappuccino et al 2008).

Preparation of the telodendrimers: We have previously published on the use of telodendrimers for NLP optimization (Luo et al). $PEG^{5k}$-$CA_8$ and related cholesterol or cholic acid based amphiphilic polymers, were prepared according to the published methods. For the telodendrimer-lipid mixtures a total of 25 mg/mL DMPC and each individual polymer were mixed at different molar ratios at an approximate 0.5-10%. The mixtures of DMPC/polymer were then sonicated for 15 min, or until optical clarity was achieved. Samples were kept on ice during the entire sonication process. After the sonication, samples were centrifuged at 13000 RCF for 2 mins to remove any metal contamination from the probe tip.

DMPC/polymer preparation: Small unilamellar vesicles of DMPC (Avanti) were prepared by probe sonication of a 25 mg/mL aqueous solution of DMPC until optical clarity was achieved; typically 15 min was sufficient. Samples were kept on ice during the sonication process. After the sonication, the samples were centrifuged at 13000 RCF for 2 minutes to remove metal contamination from the probe tip. Telodendrimes lipid mixtures were created with the above method with a total of 25 mg/mL DMPC and each individual polymer mixed at varying molar ratios between approximately 0.5-10%. 0.1% TexasRed-POPC (Invitrogen) was added to the DMPC solution before sonication if a fluorescent label on the NLP complex was desired.

Cell-free Reactions: Small-scale reactions (100 uL) or large scale (1 mL) were carried out using the Invitrogen's Expressway Maxi kit. Reaction components (Lysate, Reaction buffer, T7 Polymerase, Amino Acid Mix, and Methionine) were combined as specified by the manufacturer. 10 μg of Δ49ApoA1 DNA was added to each 1 ml reaction. To each 1 mL reaction, 2 mg DMPC/polymer mixture was then added. The reactions were incubated at 30° C., with shaking at 990 rpm for 2-18 hrs in thermomixer.

Affinity purification of NLP complexes: Immobilized metal affinity chromatography was used to isolate the protein of interest (Δ49ApoA1) from the cell-free reaction mixture. 2 ml of 50% slurry nickel-nitrilotriacetic acid Superflow resin (Qiagen) was equilibrated with PBS (50 mM Na2HP04, 300 mM NaCl, pH 8.0) under native conditions in a 10 mL capped column. Mixed the total cell free reaction (1 ml) with the equilibrated resin, and was incubated/nutated on ice for 2 hr. 1 ml of slurry and 5 mL capped column were used for the purification from small-scale reactions. The column was then washed with increasing concentrations of imidazole 10, 20 and 50 mM in the mentioned PBS buffer. Two column volumes (CV) of each wash buffer were used for a total of 6 CVs of washing. The His-tagged proteins of interest were eluted in six 1 mL fractions of 400 mM imidazole, PBS buffer. All elutions were combined, dialyzed against PBS for 18 hrs at 4° C. with stirring. After that, the combined elution was concentrated using a 100K MWCO molecular weight sieve filters (Vivascience) to a volume of ~200 uL.

Size Exclusion Chromatography: The NLPs were resolved by HPLC (Shimadzu) using a Superdex 200 10/300

GL column (GE Healthcare) with TBS running buffer (10 mM Tris pH 7.4; 0.15M NaCl; 0.25 mM EDTA, 0.005% NaN3) at a flow rate of 0.5 ml/min. The column was calibrated with four protein standards (HMW Gel Filtration Calibration kit, GE Healthcare) of known molecular weight and Stokes diameter that span the separation range of the column and the NLP samples. The void volume was established with blue dextran.

SDS PAGE: 10 µL aliquot of the purified NLPs or lipid micelles were mixed with 10 µL 2×LDS Sample buffer with reducing agents (Invitrogen), heat denatured and loaded on to a 4-12% gradient pre-made Bis-Tris gel (Invitrogen) along with the molecular weight standard NovexSharp (Invitrogen). The running buffer was IX MES-SDS (Invitrogen). Samples were electrophoresed for 38 minutes at 200V. Gels were stained with coomassie brilliant blue.

Native PAGE: 10 µL aliquot of the purified NLPs or lipid micelles were mixed with 2× native gel sample buffer (Life Technologies: Invitrogen) and loaded onto 4-12% gradient pre-made Tris-glycine gels (Life Technologies: Invitrogen). Samples were electrophoresed for 2 hours at 125 V. After electrophoresis, gels were imaged using the laser (488 nm) of a Typhoon 9410 (GE Healthcare) with a 520 nm bandpass 30 filter for the detection of the produced NLPs with incorporated FITC labeled polymer. For detection of the produced NLPs with incorporated TexasRed-POPC, the laser (532 nm) with a 610 nm bandpass 30 filter is used. Molecular weights were determined by comparing migration vs. log molecular weight of standard proteins found in the NativeMark standard (Life Technologies: Invitrogen).

Dynamic light scattering: The measurements were performed on a Nanotrac Particle Size Analyzer (Microtrac). Light from a laser diode was coupled to the sample through an optical beam splitter in the Nanotrac probe assembly. The interface between the sample and the probe was a sapphire window at the probe tip. The sapphire window reflected the original laser back through the beam splitter to a photodetector. This signal with the same frequency as the original laser acted as a reference signal for detection, offering heterodyne detection. The laser passed through the sapphire window and was scattered by the particles, which were in suspension but moving under Brownian motion. The laser was frequency shifted according to the Doppler Effect relative to the velocity of the particle. Light was scattered in all directions including 180 degrees backwards. This scattered, frequency shifted light was transmitted through the sapphire window to the optical splitter in the probe to the photodetector. These signals of various frequencies combined with the reflected signal of un-shifted frequency (Controlled Reference) to generate a wide spectrum of heterodyne difference frequencies. The power spectrum of the interference signal was calculated. The power spectrum was then inverted to give the particle size distribution.

Cryo Transmission Electron Microscopy. All samples were preserved as a frozen hydrated specimen in the presence of saturated ammonium molybdata and examined with a JEOL JEM-2100F transmission electron microscope at magnification of 80,000× under liquid nitrogen temperature. Clusters of NLPs were found with plain NLP sample, while only a few clusters of NLPs were found with telodendrimer NLPs. Majority of the NLPs are shown inside views. A few of them appeared in their top view. Tobacco mosaic virus (TMV) was added as reference to indicate the quality of cryo-EM preparation, as well as the internal calibration of microscope magnification. The size of the nanoparticles varied from 10 nm to 15 nm.

Solution Phase Characterization using Flourescent Correlation Spectroscopy (FCS). Characterization of nano-particles and their dynamic shape and association in solution remains a challenge, which we have addressed using FCS performed on a MicroTime 200 single molecule fluorescence lifetime measurement system (PicoQuant). FCS is capable of measuring molecular diffusion statistics in solution with sensitivity for single molecule fluorescence. This allows us to rapidly and accurately determine the hydrodynamic radii of the newly formed nano-complexes in an aqueous environment. Complimentary techniques such as dynamic light scattering (DLS) performed on a Nanotrac Particle Size Analyzer (Microtrac) and potentially atomic force microscopy (AFM) can be used to further validate FCS data.

TABLE 1

NLP size and level of aggregation with and without telodendrimers.

| Additive | M.W.[a] | NLP size (nm)[b] | S.D.[c] | Aggregate %[d] | µg/mL |
|---|---|---|---|---|---|
| PEG$^{2K}$_D-CA$_4$ | 4 kDa | 6.76 | 0.30 | 0.00 | |
| PEG$^{2K}$_D-CA$_8$ | 6 kDa | 13.32 | ND | 1.00 | |
| PEG$^{5K}$_D-CF$_4$ | 7 kDa | 27.14 | 5.32 | 15.00 | 750 |
| PEG$^{5K}$_D-CF$_8$ | 9 kDa | 17.58 | 4.59 | 16.00 | |
| DMPC | 0.68 kDa | 40.30 | 1.27 | 100.00 | 190 |

[a]Molecular weight of additive telodendrimer or lipid alone.
[b]Resulting size of monodispersed NLPs as measured by Dynamic light scatter.
[c]Standard deviation between replicate experiments.
[d]Dynamic light scattering measure of aggregated material.

Results

Telodendrimer addition increases the soluble yield of nanoparticles. A total of 1 ml of cell-free reaction with and without telodendrimer were used to compare protein yield and solubility of the NLP product (FIGS. 1A-1B). Several types of telodendrimers were utilized as depicted in Table 1. Telodendrimer molecules used included: PEG$^{2k}$-CA$_4$ containing 4 cholic acid molecules linked to a single linear PEG chain (2 kDa); PEG$^{2k}$-CA$_8$ containing 8 cholic acid molecules linked to a single linear PEG chain (2 kDa); PEG$^{5k}$-CF$_4$ containing 4 cholesterol molecules linked to a single linear PEG chain (5 kDa); PEGs$^{5k}$-CA$_8$ containing 8 cholic acid molecules linked to a single linear PEG chain (5 kDa). A 4-12% SDS-PAGE gel was used to separate the products and nickel affinity chromatography was used for purification. The profile of NLP or telodendrimer conjugated NLP is shown in FIGS. 2A-2B. We noted a 2-4 fold increase of soluble telodendrimer conjugated NLP produced when compared to NLP alone. As seen in FIGS. 2A-2B, the PEG$^{5k}$-CA$_8$ telodendrimer reaction yielded approximately 750 ug/mL of Telo-NLP, compared to 190 ug/mL of NLP alone. This difference appeared to be independent of the total amount of delta-ApoA1 protein produced.

Figure 3A:
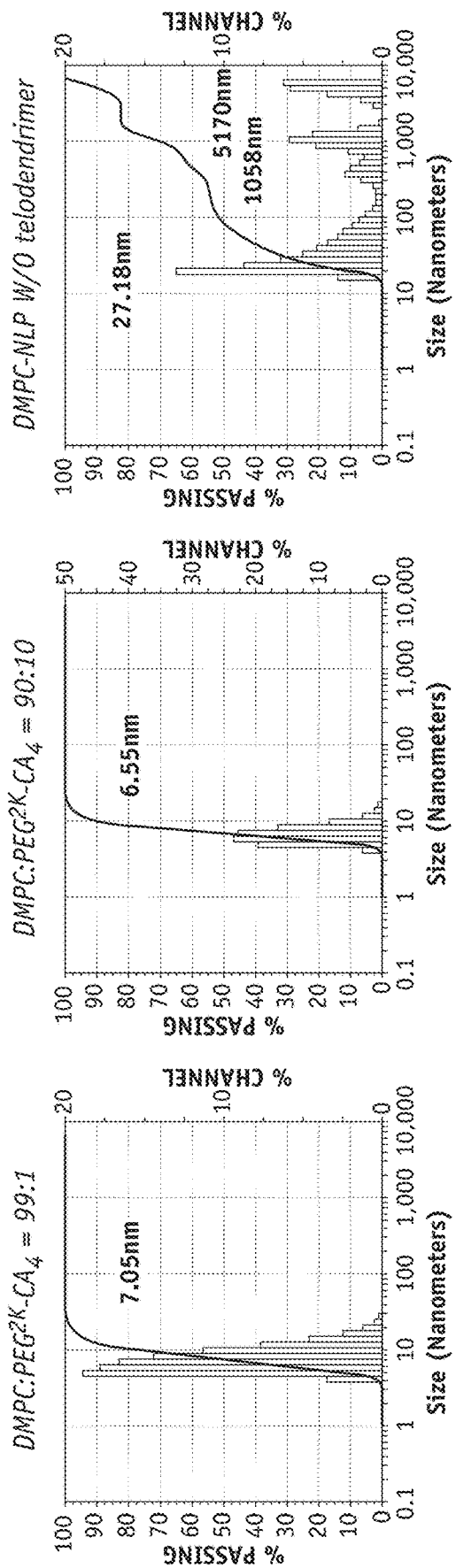
FIGS. 3A-3C show telodendrimer addition to nanoparticle formation changed aggregation levels and size tenability. Dynamic Light Scattering (DLS) was used to assess several biophysical properties of the Telo-NLP particles.
Figure 3B:
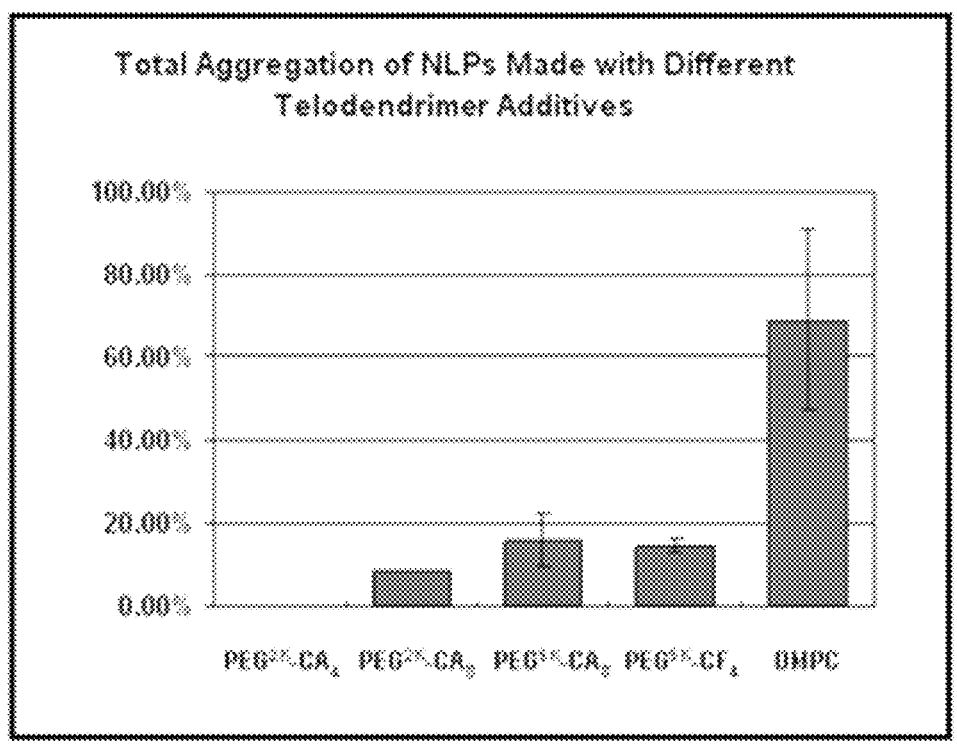
Figure 3C:
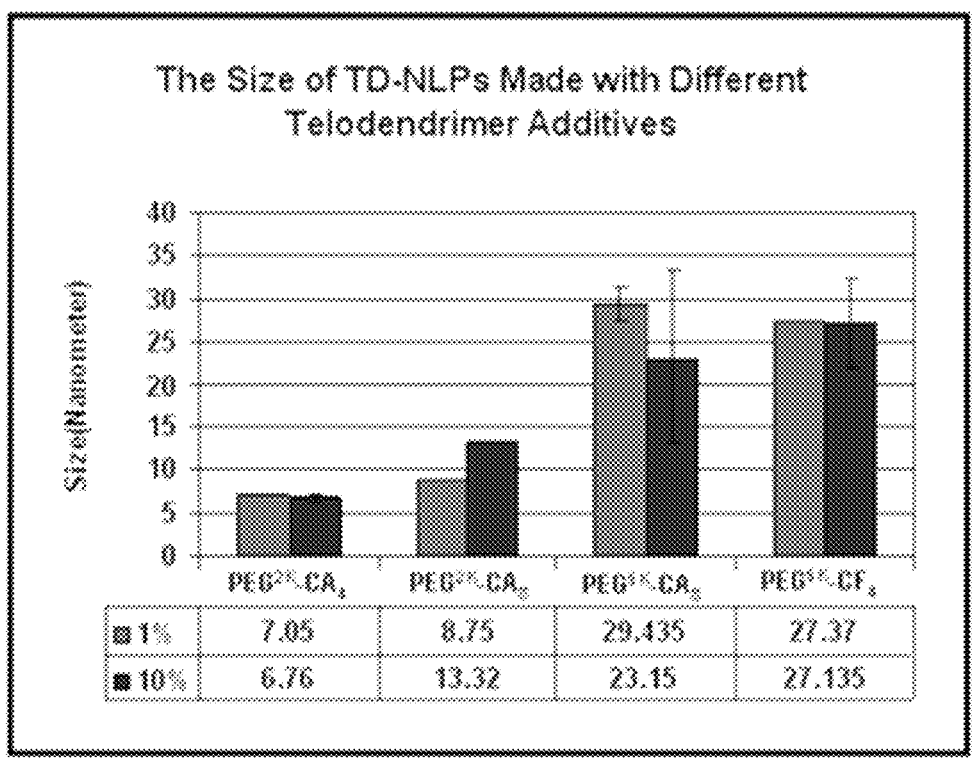

Telodendrimers impacted the size and level of aggregation of nanoparticles. Dynamic light scattering (DLS) was used to evaluate the size and monodispersity of the NLPs compared to Telo-NLPs. The overall size of the NLPs were dependent upon the length of the incorporated PEG molecule. The PEG$^{2k}$ Telo-NLPs ranged in size from 7 to 13 nm, while the PEG$^{5k}$Telo-NLPs were 15 to 30 nm in diameter based on DLS traces (FIG. 3C). Previously reported studies have shown that NLPs alone measure approximately 8 nm in solution when dispersed (Gao et al., 2011). Changing the amount of telodendrimer added to the NLP assembly process over a range of 1-10% of total lipid did not significantly alter the overall size of the Telo-NLPs (FIGS. 3A and 3C).

NLP aggregation appears to be size dependent, with larger telodendrimer molecules exhibiting higher levels of aggregation. The overall level Telo-NLPs aggregation rate was reduced 10-100 times compared to NLPs assembled only in the presences of DMPC alone (FIGS. 3A-3B). Increases in the amount of telodendrimer to lipid ratio (>10%), was associated with greater levels of aggregation (data not shown). There were no significant changes in NLP size or aggregation when adjusting for telodendrimers containing cholate or cholesterol head groups over the 1-10% telodendrimer to lipid ratio.

Figure 4D:
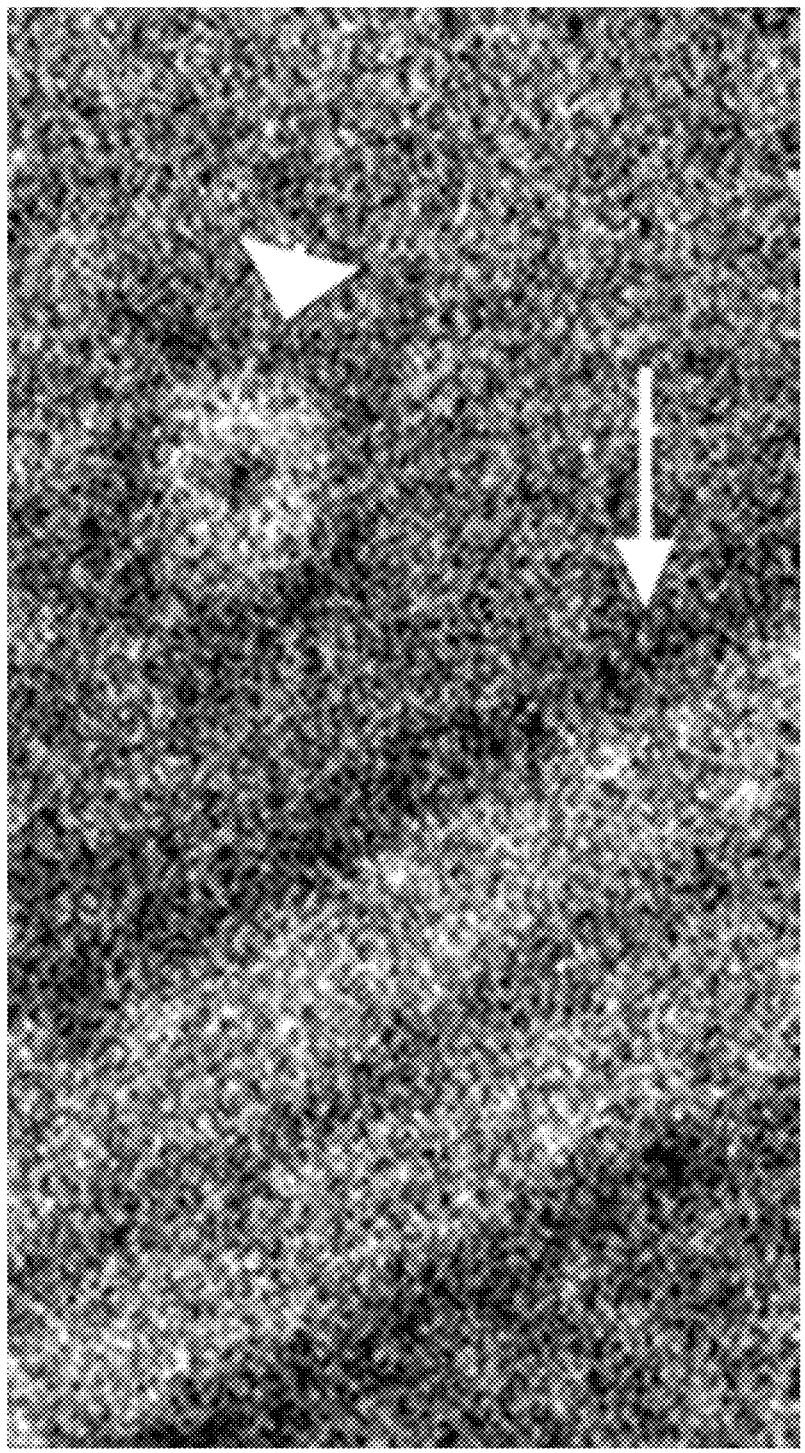

Telo-NLP complexes are disc like in shape. FIGS. 4A-4D illustrate in Cryo TEM images that NLPs are discoidal in shape with height dimensions consistent with previously published images of NLPs and nanodisc that are based on phospholipid bilayers with diameters averaging about 10 nm. Three assemblies are shown in FIGS. 4A-4C, with DMPC alone (FIG. 4A) and two types of telodendrimers (FIGS. 4B-4C). Unlike previous reports, NLPs alone (FIG. 4A) in our study exhibited large clustering rather than stacked particles, or "rouleaux," which may be attributable to the inclusion of tobacco virus particles in this study.

Figure 5:
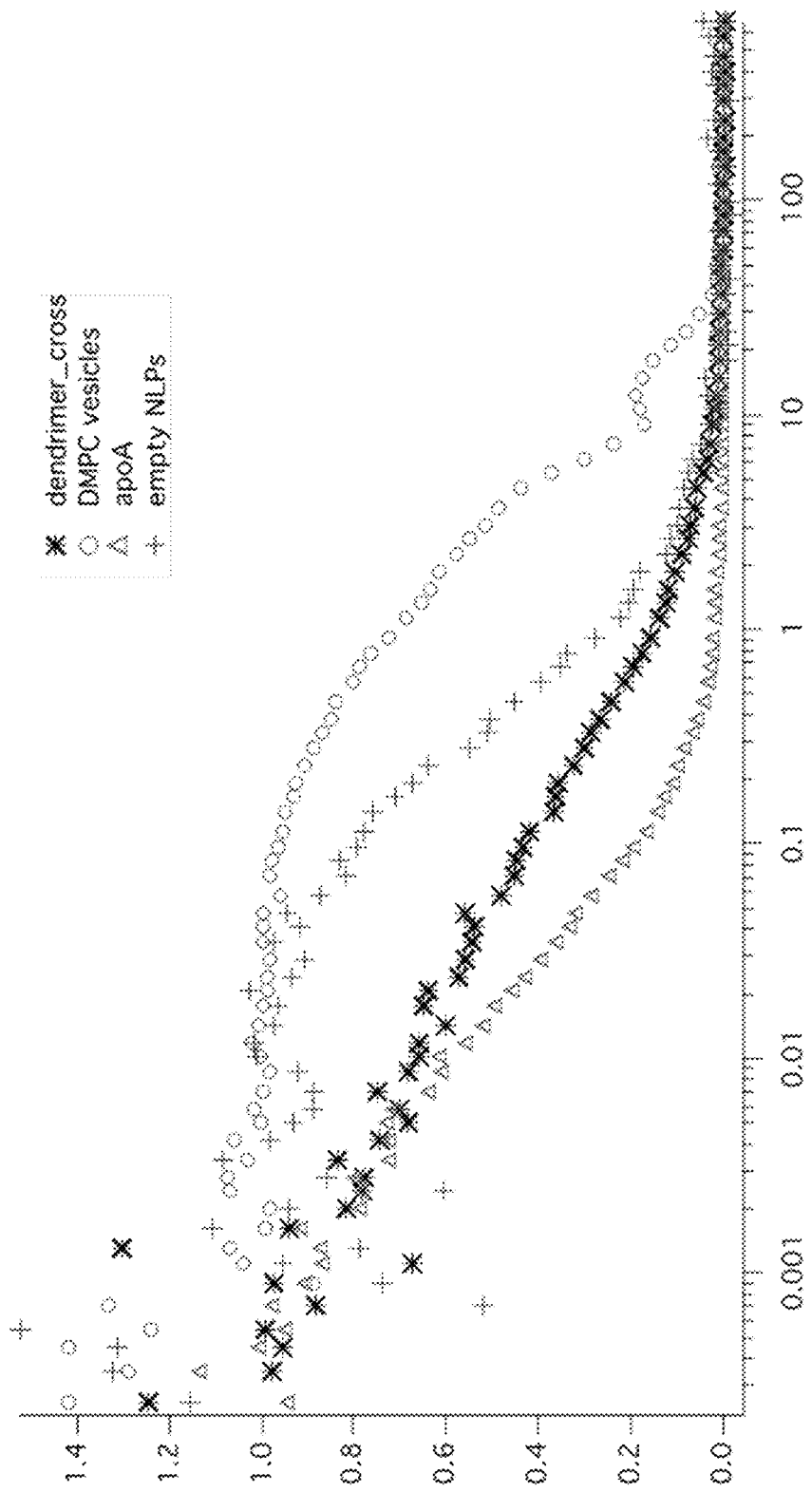
FIG. 5 shows the telodendrimers are associated with nanoparticles as a complex. Diffusion curves of proteins and NLP/Telo-NLP complexes as measured by FCS. The curves correspond to Δ49A1 (triangle). Telo-NLP (star), NLP (plus) and DMPC (circle) vesicles in 1×PBS respectively.

FCS analysis has been used to topologically confirm telodendrimer association and labeling of NLP (Gao et. al 2011). Cell-free reactions were used to assemble NLPs tagged with Bodipy®-FL, which included Texas Red labels within the complex. As seen in FIG. 5, both NLP and Telo-NLP complex (identified by cross-correlating Bodipy/FITC and Texas Red in the complex) diffused significantly faster than DMPC vesicles alone, but slower than the protein Δ49ApoA1 (apolipoprotein without any DMPC). In addition, native gel electrophoresis was used to compare the molecular weight of NLPs to Telo-NLPs. The size of the NLPs approximated 240 kDa (data not shown), which was consistent with the FCS analysis.

Figure 6A:
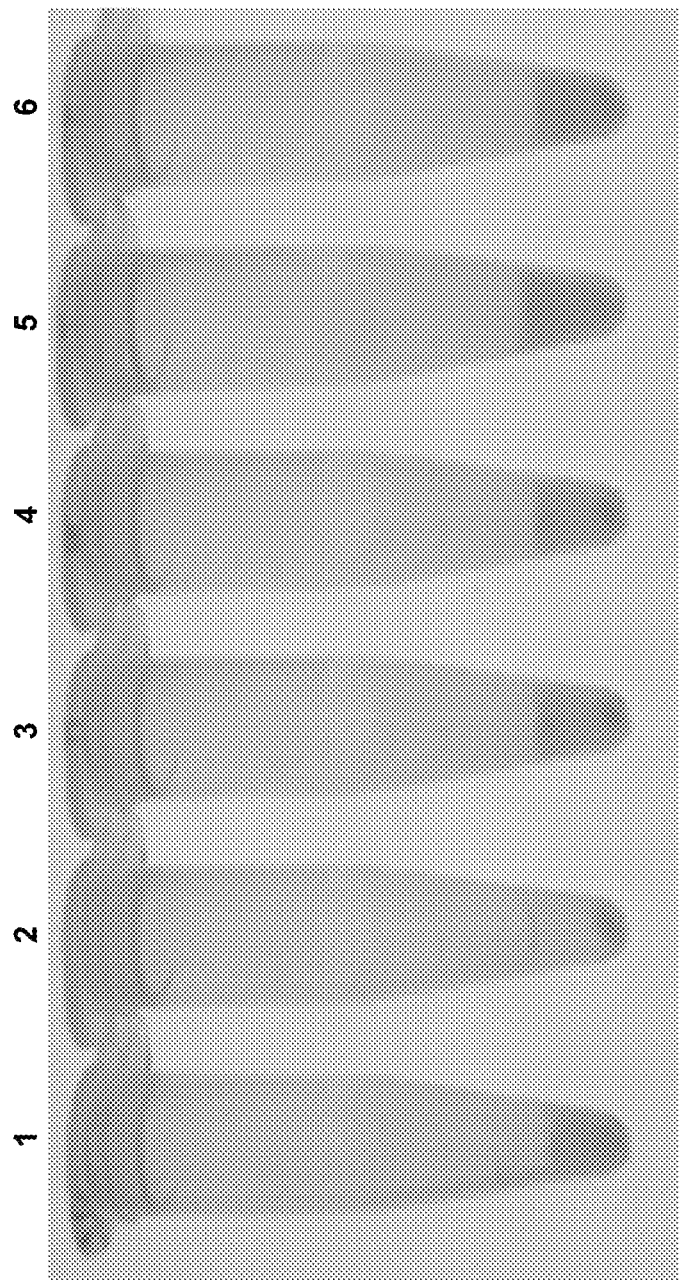
FIGS. 6A-6B show the telodendrimers are compatible with membrane protein production. The cell free reactions are setup with 1 ug/mL pIVEX-2.4b-apoA1 and 10 ug/mL pIVEX-2.4b-boP and 2 mg/mL lipid (100% DMPC or 99.5% DMPC and 0.5% telodendrimer, molar ratio), BODIPY-FL and 50 uM all trans retinal, 30 C at 990 rpm for 4 hours.
Figure 6B:
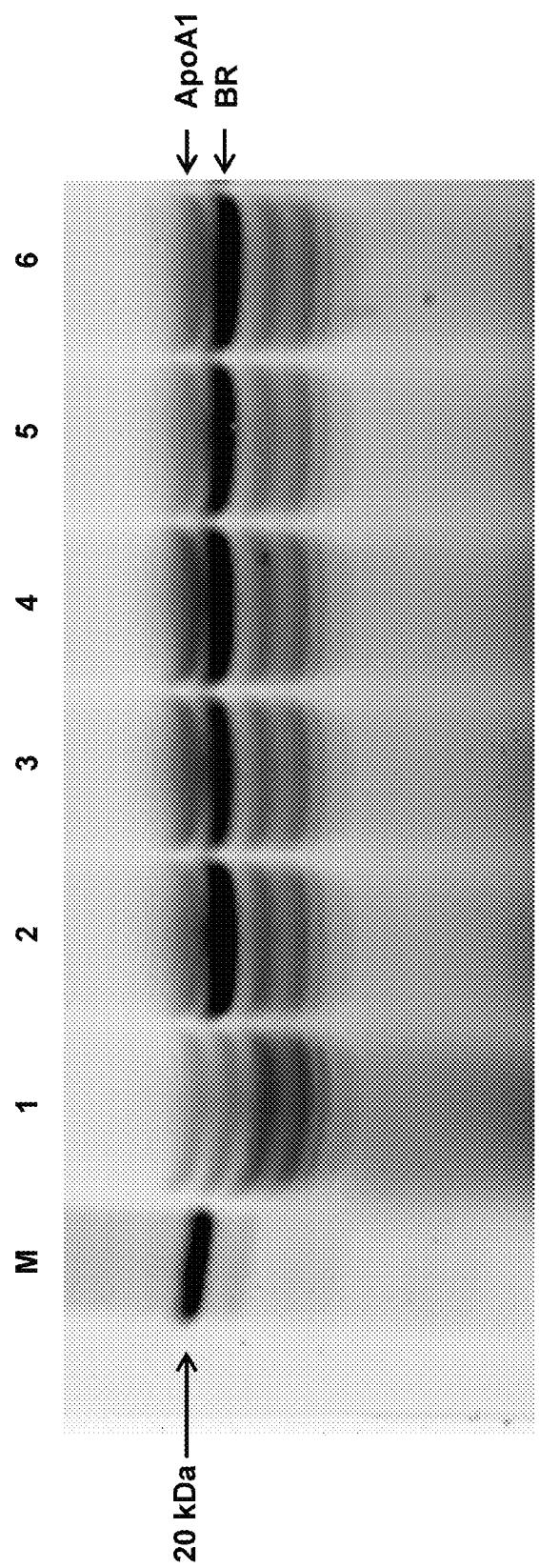

Telo-NLPs support incorporation of functional intergral membrane proteins. It has been previously shown, that bacteriorhodopsin (bR; a seven transmembrane helical protein, from *Halobacterium salinarium*) can be robustly co-expressed and assembled into NLPs for biophysical characterization Cappuccino et al. 2008; Katzen et al., 2008; Gao et al., 2011). In this study, assembly of the soluble bR-NLP complex was observed within 4 h after addition of plasmids to an *E. coli* cell-free lysate (FIG. 6A). Addition of telodendrimers to the cell-free reaction did not affect bR function as indicated by the pink coloration of the tubes, which is an indication of proper folding and function. Production of similar amounts of total bR protein with and without telodendrimers was also observed (FIG. 6B).

Telodendrimer addition can increase the soluble yield of nanoparticles. A total of 1 ml of cell-free reactions with and without Telodendrimer DMPC were used to compare protein yield as well as solubility for NLP purification (FIG. 1A). Several different types of telodendrimers as shown in Table 1. Telodendrimer molecules used were: $PEG^{2k}$-$CA_4$ containing 4 Cholesterol molecules linked to a single linear PEG molecule (2 kDa); $PEG^{2k}$-$CA_8$) containing 8 Cholesterol molecules linked to a single linear PEG molecule (2 kDa); $PEG^{5k}$-$CF_4$ containing 4 cholic acid molecules linked to a single linear PEG molecule (5 kDa); $PEG^{5k}$-$CF_8$ containing 8 cholic acid molecules linked to a single linear PEG molecule (5 kDa). A 4-25% SDS-PAGE gel was used to generate a typical profile for a NLP or Telo-NLP purification using nickel affinity chromatography as shown in FIGS. 2A-2B. In typical reactions a general increase of 2-4 fold of soluble Telo-NLPLs was noted compared to NLPs alone. For example using the $PEG^{5k}$-$CF_K$ telodendrimer yielded approximately 750 ug/mL of Telo-NLP compared to 190 ug/mL of NLP. This difference did not appear to be related to the total amount of delta-ApoA1 protein produced, see FIGS. 2A-2B lanes containing total protein lysates from the cell-free reaction. This appears to reflect increase in the amount of soluble NLP produced by the addition of the telodendrimer (See FIGS. 2A-2B, elution lanes).

Telodendrimers impact the size and level of aggregation level of nanoparticles. Dynamic light scattering (DLS) was used to look at the size and general monodispersity of the NLPs compared to the Telo-NLPs. The telodendrimer molecules impacted the size of the nanolipoprotein particles depending on the length of the PEG linear molecule. Table 1, list the DLS diameters and levels of aggregation. The $PEG^{2k}$ molecules ranged in size between 7 and 13 nm, while the $PEG^{5k}$Telo-NLPs were 18-27 nm in diameter based on DLS traces (FIGS. 3A-3C). The known diameter of the NLPs alone was 40 nm, but this size was most likely due to the level of aggregation of the samples, which was consistently seen across replicate experiments. Previously reported studies have shown that NLPs are around 8 nm in solution when dispersed. There was also a size dependence for the level of aggregation with the larger telodendrimer molecules having a higher level of aggregation. Interestingly, these levels were 10-100 times less than the level of aggregation seen in the NLP alone sample. Thus indicating an increased monodispersity by inclusion of the telodendrimers in the cell-free reactions. Altering the amount of telodendrimer added to the NLP assembly process over a range of 0.5-10% of total lipid did not alter the general size of the Telo-NLPs (FIGS. 4A-4D). However, greater increases (>10%) in the amount of telodendrimer to lipid ratio did cause greater levels of aggregation. No significant change was observed in the size or aggregation level for the difference in the number of cholate or cholesterol tails over the 0.5-10% ratio.

Telo-NLP complexes are disc like in shape. A. FIG. 5, show NLPs whose dimensions are consistent with previously described observations. Three of these assemblies made are shown, with DMPC (FIG. 4A) and two different assemblies with telodendrimers (FIG. 4B). Unlike previous reports, we observed large clustering of the NLPs rather than stacked particles—described as "rouleaux". Combined, EM data suggests discoidal structures with height dimensions consistent with a phospholipid bilayer and a diameter of about 10-25 nm. Telodendrimer addition during assembly clearly changed the aggregation status of the particles as shown in FIG. 5.

FCS analysis was also used to compare the NLP assemblies and demonstrate that the telodendrimer molecules were associated with the NLP. Importantly, FCS can also be used to illustrate labeling of the NLP via the telodendrimer and to potentially confirm other topological features of the particles. Cell-free were assembled NLPs tagged with Bodipy®-FL and included Texas Red labels within the complex. The Telo-NLPs were labelled with FITC directly coupled to the telodendrimers and included Texas Red labels on the lipids. As seen in FIGS. 6A-6B, both the NLP and Telo-NLP complex (identified by cross-correlating Bodipy and Texas Red in the complex) diffused significantly faster than DMPC vesicles alone. However, this diffusion time was also significantly slower than Δ49A1 (apolipoprotein without any DMPC), providing further evidence for the complex formation.

Figure 7:
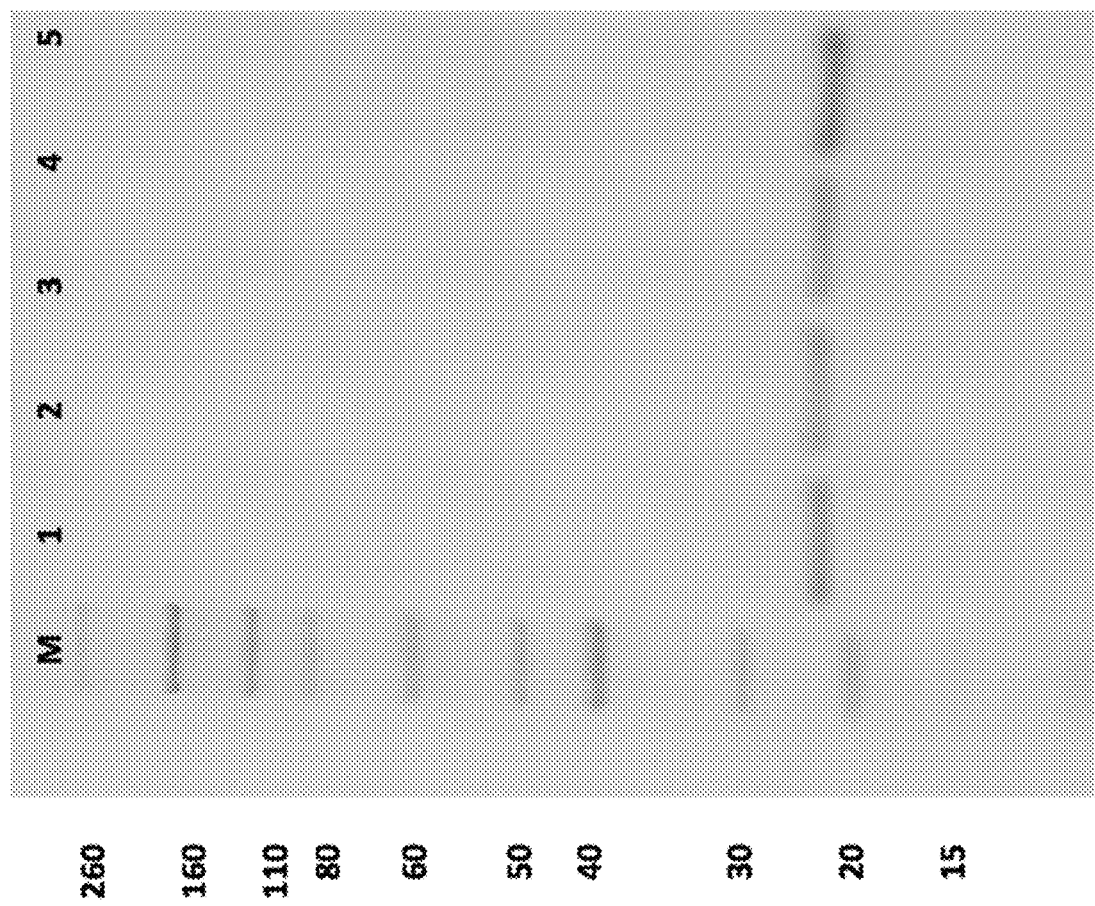
FIG. 7 shows an SDS-PAGE analysis using PEG$^{2k}$-CA$_4$ (lane 1), PEG$^{5k}$-CF$_4$ (lane 2), PEG$^{5k}$-CF$_8$ (lane 3) and PEG$^{10k}$-CF$_4$ (lane 4), which demonstrates that the telodendrimer-nanolipoproteins are >90% homogenous.
Figure 8:
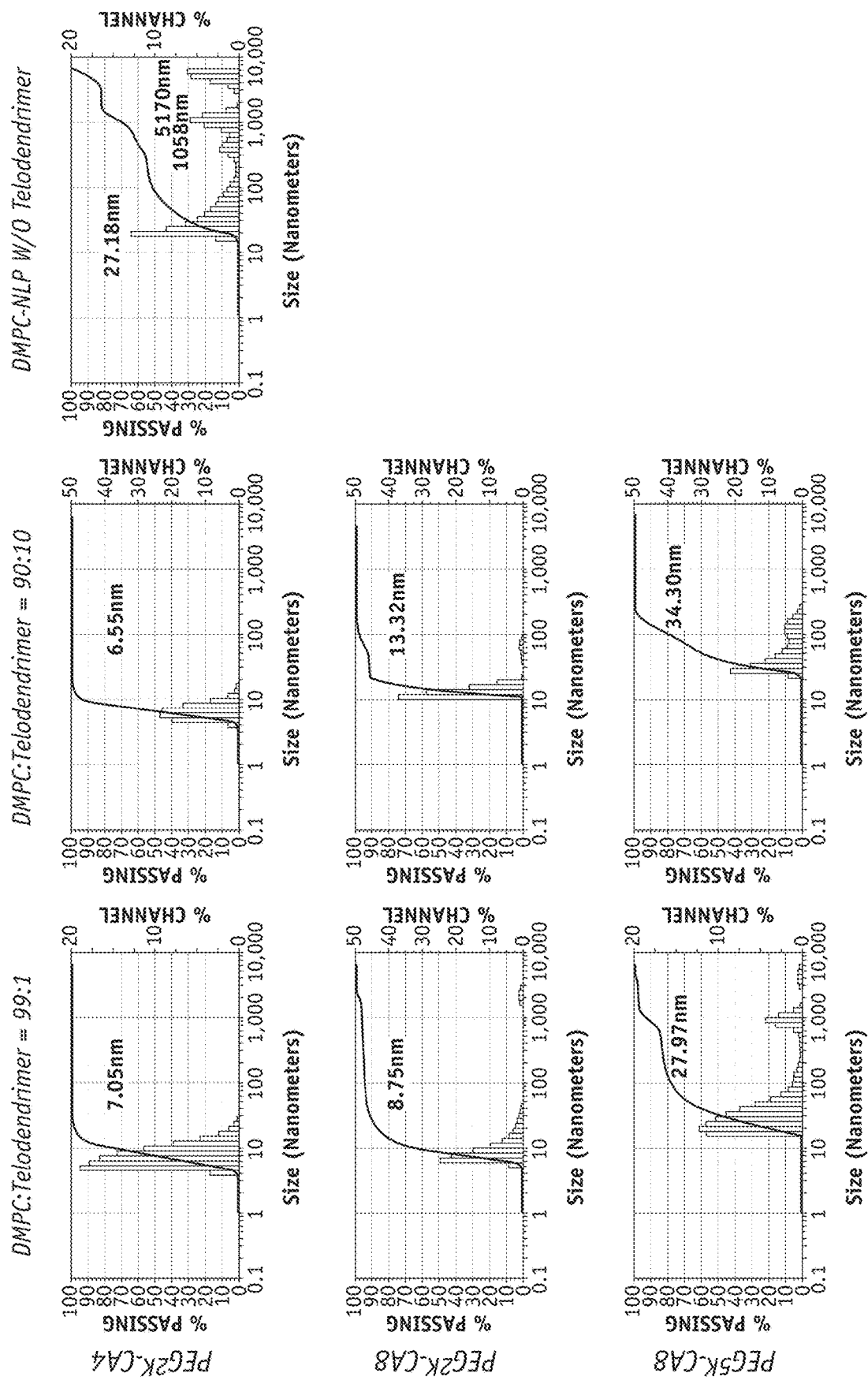
FIG. 8 provides a comparison of telodendrimer-nanolipoprotein size and aggregation using 1% and 10% levels of telodendrimer for PEG$^{2k}$-CA$_4$, PEG$^{2k}$-CA$_8$, PEG$^{5k}$-CA$_8$, PEG$^{5k}$-CF$_4$ and PEG$^{10k}$-CF$_4$
Figure 8:
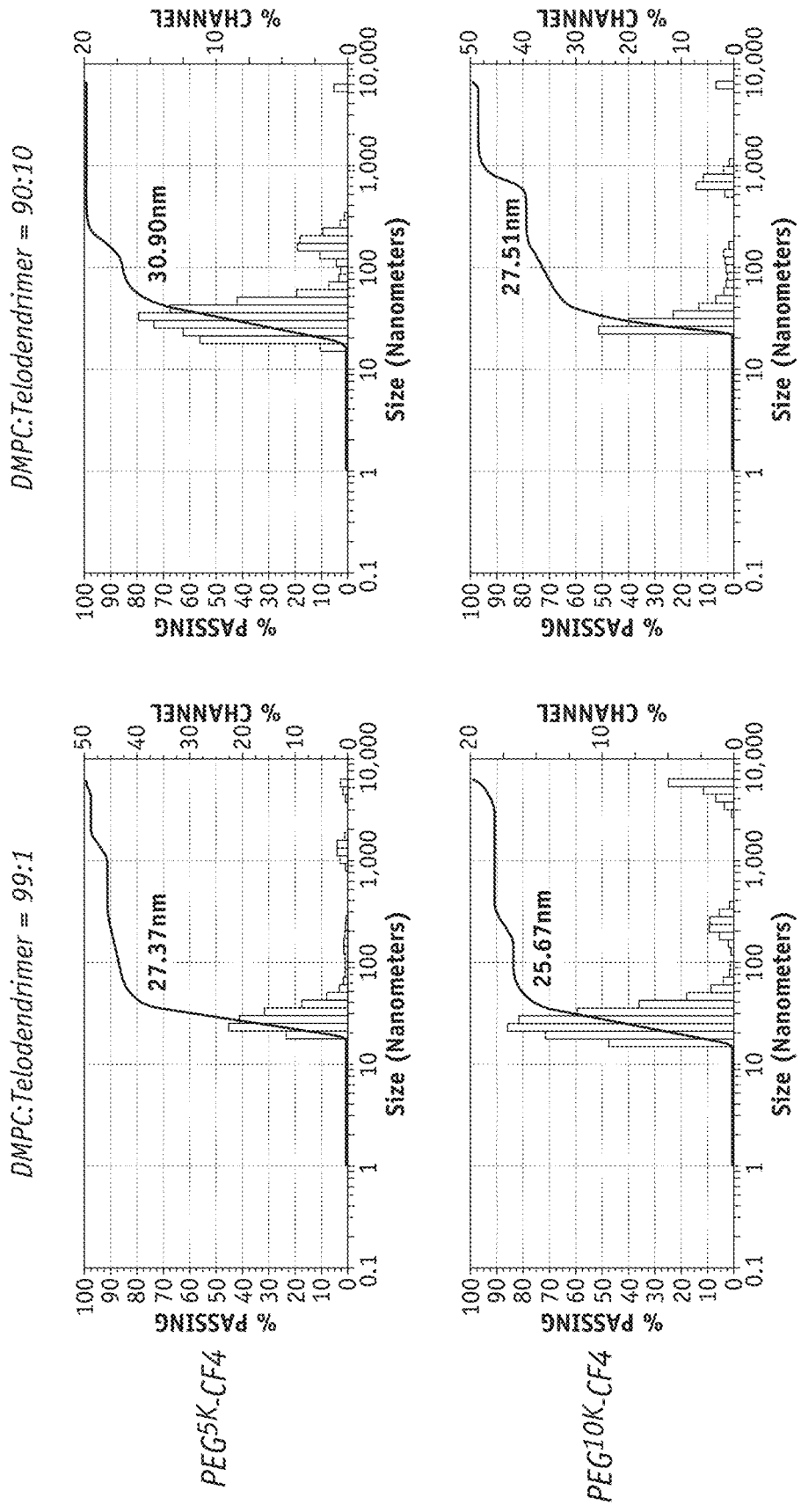
Figure 9:
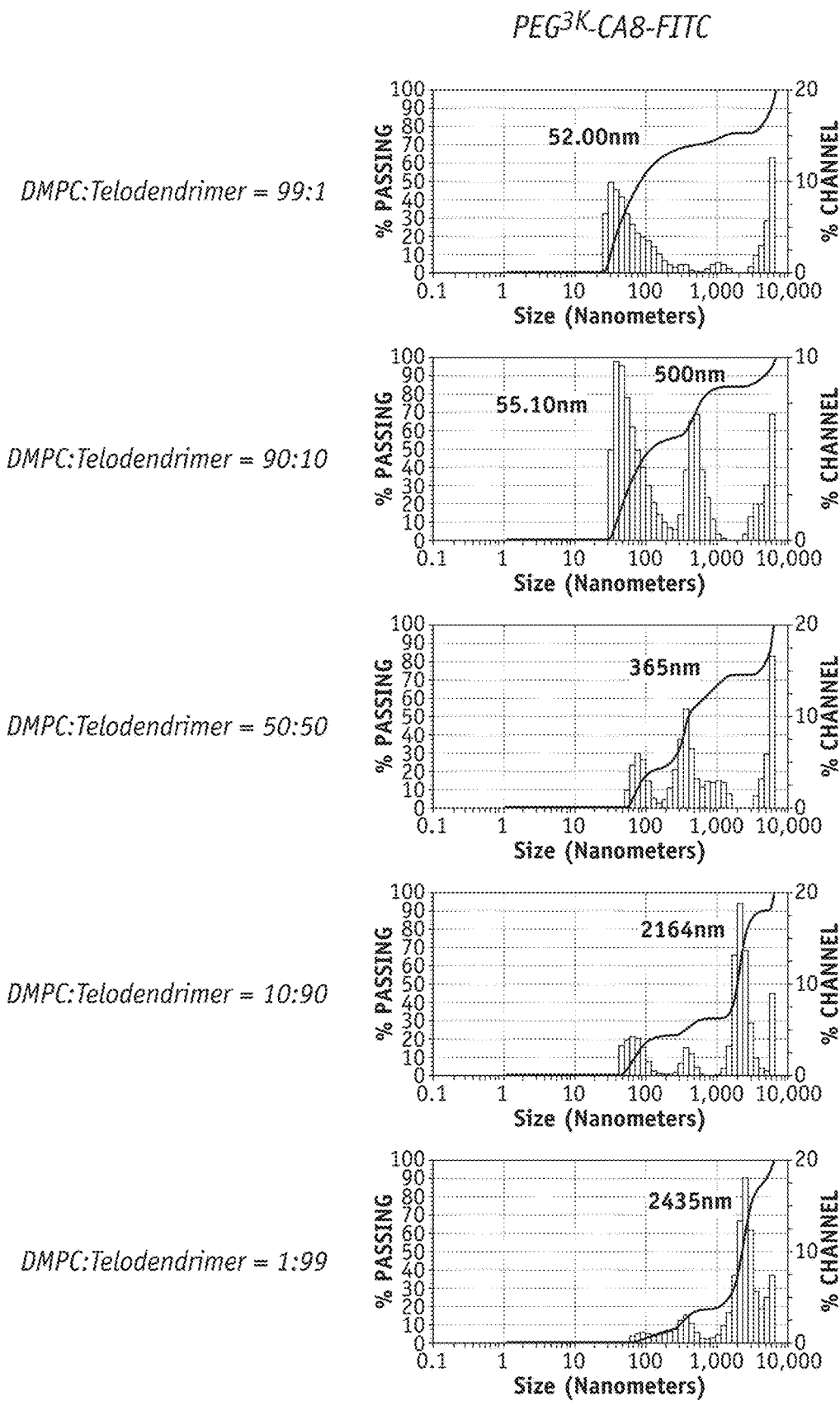
FIG. 9 shows aggregation of telodendrimer-nanolipoprotein for PEG$^{3k}$-CA$_8$-FITC with ratios of DMPC to telodendrimer of 99:1, 90:10, 50:50, 10:90 and 1:99.

Telo-NLPs support assembly of a functional membrane protein. Assembly of the soluble bacteriorhodopsin-NLP (bR-NLP) complex was observed within 4 h after addition of plasmids to an *E. coli* cell-free lysate (FIG. 7). Addition of telodendrimers to the cell-free reaction did not inhibit bacteriorhodopsin (bR) function as indicated by pink coloration of the tubes. The coloration is an indicator of function because it only occurs with proper folding and function of bR. The results indicated production of similar amounts of total bR protein produced with or without telodendrimers. As previously reported, the size range of NLPs was approximately 240 kDa with a smear on the gel that represented a heterogeneous size distribution, where Telo-NLP complex were slightly larger than NLPs alone. Some Telo-NLP complex heterogeneity was also observed by native gel electrophoresis. This heterogeneity may have been due to multiple telodendrimer interactions within the NLPs, which could potentially modify protein-lipid interactions.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate. Further, the computer readable form of the sequence listing of the ASCII text file IL-12539C2C1-P1799-USCC-Seq-List-ST25 is incorporated herein by reference in its entirety.

SEQUENCES

SEQ ID NO: 1 (*Homo sapiens* apolipoproteinA-1 (APOA1), cDNA, NM_000039.1)
AGAGACTGCGAGAAGGAGGTCCCCCACGGCCCTTCAGGATGAAAGCTGC
GGTGCTGACCTTGGCCGTGCTCTTCCTGACGGGGAGCCAGGCTCGGCAT
TTCTGGCAGCAAGATGAACCCCCCCAGAGCCCCTGGGATCGAGTGAAGG
ACCTGGCCACTGTGTACGTGGATGTGCTCAAAGACAGCGGCAGAGACTA
TGTGTCCCAGTTTGAAGGCTCCGCCTTGGGAAAACAGCTAAACCTAAAG
CTCCTTGACAACTGGGACAGCGTGACCTCCACCTTCAGCAAGCTGCGCG
AACAGCTCGGCCCTGTGACCCAGGAGTTCTGGGATAACCTGGAAAAGGA
GACAGAGGGCCTGAGGCAGGAGATGAGCAAGGATCTGGAGGAGGTGAAG
GCCAAGGTGCAGCCCTACCTGGACGACTTCCAGAAGAAGTGGCAGGAGG
AGATGGAGCTCTACCGCCAGAAGGTGGAGCCGCTGCGCGCAGAGCTCCA
AGAGGGCGCGCGCCAGAAGCTGCACGAGCTGCAAGAGAAGCTGAGCCCA
CTGGGCGAGGAGATGCGCGACCGCGCGCGCGCCCATGTGGACGCGCTGC
GCACGCATCTGGCCCCCTACAGCGACGAGCTGCGCCAGCGCTTGGCCGC
GCGCCTTGAGGCTCTCAAGGAGAACGGCGGCGCCAGACTGGCCGAGTAC
CACGCCAAGGCCACCGAGCATCTGAGCACGCTCAGCGAGAAGGCCAAGC
CCGCGCTCGAGGACCTCCGCCAAGGCCTGCTGCCCGTGCTGGAGAGCTT
CAAGGTCAGCTTCCTGAGCGCTCTCGAGGAGTACACTAAGAAGCTCAAC
ACCCAGTGAGGCGCCCGCCGCCGCCCCCCTTCCCGGTGCTCCAGAATAA
ACGTTTCCAAAGTGGG SEQ ID NO: 2 (*Homo sapiens* Δ49 apolipoproteinA-1 (Δ49A1), cDNA)
AGCGGCAGAGACTATGTGTCCCAGTTTGAAGGCTCCGCCTrGGGAAAAC
AGCTAAACCTAAAGCTCCTTGACAACTGGGACAGCGTGACCTCCACCTT
CAGCAAGCTGCGCGAACAGCTCGGCCCTGTGACCCAGGAGTTCTGGGAT
AACCTGGAAAAGGAGACAGAGGGCCTGAGGCAGGAGATGAGCAAGGATC
TGGAGGAGGTGAAGGCCAAGGTGCAGCCCTACCTGGACGACTTCCAGAA
GAAGTGGCAGGAGGAGATGGAGCTCTACCGCCAGAAGGTGGAGCCGCTG
CGCGCAGAGCTCCAAGAGGGCGCGCGCCAGAAGCTGCACGAGCTGCAAG
AGAAGCTGAGCCCACTGGGCGAGGAGATGCGCGACCGCGCGCGCGCCCA
TGTGGACGCGCTGCGCACGCATCTGGCCCCCTACAGCGACGAGCTGCGC
CAGCGCTTGGCCGCGCGCCTTGAGGCTCTCAAGGAGAACGGCGGCGCCA
GACTGGCCGAGTACCACGCCAAGGCCACCGAGCATCTGAGCACGCTCAG
CGAGAAGGCCAAGCCCGCGCTCGAGGACCTCCGCCAAGGCCTGCTGCCC
GTGCTGGAGAGCTTCAAGGTCAGCTTCCTGAGCGCTCTCGAGGATACAC
TAAGAAGCTCAACACCCAGTGAGGCGCCCGCCGCCGCCCCCCTTCCCGG
TGCTCAGAATAAACGTTTCCAAAGTGGG SEQ ID NO: 3 (*Homo sapiens* apolipoproteinA-1 (APOA1), protein, NP_000030.1)
MKAAVLTLAVLFLTGSQARHFWQQDEPPQSPWDRVKDLATVYVDVLKDS
GRDYVSQFEGSALGKQLNLKLLDNWDSVTSTFSKLREQLGPVTQEFWDN
LEKETEGLRQEMSKDLEEVKAKVQPYLDDFQKKWQEEMELYRQKVEPLR
AELQEGARQKLHELQEKLSPLGEEMRDRARAHVDALRTHLAPYSDELRQ
RLAARLEALKENGGARLAEYHAKATEHLSTLSEKAKPALEDLRQGLLPV
LESFKVSFLSALEEYTKKLNTQ SEQ ID NO: 4 (*Homo sapiens* Δ49 apolipoproteinA-1 (Δ49A1), protein)
SGRDYVSQFEGSALGKQLNLKLLDNWDSVTSTFSKLREQLGPVTQEFW
DNLEKETEGLRQEMSKDLEEVKAKVQPYLDDFQKKWQEEMELYRQKVE
PLRAELQEGARQKLHELQEKLSPLGEEMRDRARAHVDALRTHLAPYSD
ELRQRLAARLEALKENGGARLAEYHAKATEHLSTLSEKAKPALEDLRQ
GLLPVLESFKVSFLSALEEYTKKLNTQ

What is claimed is:

1. A nanodisc comprising:
   a membrane scaffold protein;
   a telodendrimer;
   a lipid; and
   a hydrophobic drug.

2. The nanodisc of claim 1, wherein the membrane scaffold protein is apolipoprotein.

3. The nanodisc of claim 1, wherein the telodendrimer has the formula:

PEG-D-(R)n wherein
   D is a dendritic polymer having a single focal group and a plurality of end groups;
   PEG is polyethyleneglycol (PEG) of 1-100 kDa linked to the focal group of the dendritic polymer;
   each R is independently selected from the group consisting of the end group of the dendritic polymer and an amphiphilic compound, such that when R is not an end group each A is linked to one of the end groups; and
   subscript n is an integer from 2 to 20, wherein subscript n is equal to the number of end groups on the dendritic polymer, and wherein at least half the number n of R's are each an amphiphilic compound.

4. The nanodisc of claim 3, wherein the dendritic polymer is a poly(lysine) dendritic polymer wherein each end group is hydroxy.

5. The nanodisc of claim 3, wherein each amphiphilic compound is cholic acid (CA).

6. The nanodisc of claim 5, wherein the telodendrirner is selected from the group consisting of $PEG^{5k}$-D-$CA_8$, $PEG^{5k}$-D-$CA_4$ and $PEG^{2k}$-D-$CA_4$, wherein each dendritic polymer D is a poly(lysine) dendritic polymer wherein each end group is hydroxy.

7. The nanodisc of claim 1, wherein the lipid is selected from the group consisting of a phospholipid, cholesterol, a phosphatidylcholine, a phosphatidylethanolamine, a phosphatidylglycerol, a phosphatidylserine, and a phosphatidylinositol.

8. The nanodisc of claim 7, wherein the lipid is selected from the group consisting of 1,2-dipalmitoyl-sn-glycero-3-phosphocholine (DPPC), 1,2-ditetradecanoyl-sn-glycero-3-phosphocholine (DMPC), 1-tetradecanoyl-2-hexadecanoyl-sn-glycero-3-phosphocholine (MPPC), 1,2-dioctadecanoyl-sn-glycero-3-phosphocholine (DSPC), 1,2-distearoyl-sn-glycero-3-phosphoethanolamine (DSPE), 1,2-dihexadecanoyl-sn-glycero-3-phosphoethanolamine (DPPE), 1,2-distearoyl-sn-glycero-3-phospho-(1'-rac-glycerol) (DSPC), 1,2-dipalmitoyl-sn-glycero-3-phospho-(1'-rac-glycerol) (DPPG), 1-tetradecanoyl-2-hexadecanoyl-sn-glycero-3-phosphoglycerol (MPPG) and cholesterol.

9. The nanodisc of claim 7, wherein the lipid is DMPC.

10. The nanodisc of claim 1, wherein the nanodisc is less than about 100 nm in size.

11. The nanodisc of claim 1, wherein the nanodisc is less than about 10 nm in size.

12. The nanodisc of claim 1, herein the ratio of lipid to telodendrimer is from about 200:1 to about 5:1 (w/w).

13. The nanodisc of claim 1, wherein the ratio of lipid to telodendrimer is about 9:1 (w/w).

14. A cell-free method of making a nanodisc, the method comprising:
    forming a vesicle comprising a telodendrimer and a lipid, wherein the ratio of lipid to telodendrimer is from about 500:1 to about 1:1 (w/w); and
    forming a reaction mixture of the vesicle and a membrane scaffold protein in the absence of a cell, thereby preparing the nanodisc
    the method further comprising
    incorporating a hydrophobic drug in the reaction mixture and/or
    loading the hydrophobic drug into the nanodisc.

15. The method of claim 14, wherein the membrane scaffold protein is apolipoprotein.

16. The method of claim 14, wherein the reaction mixture further comprises a lysate, a buffer, and a polymerase.

17. The method of claim 14, wherein the lipid:telodendrimer are present in a ratio of about 99:1 (w/w).

18. The method of claim 14, wherein the lipid:telodendrimer are present in a ratio of about 9:1 (w/w).

19. The nanodisc of claim 1, wherein the hydrophobic drug is embedded within the nanodisc.

* * * * *